US008202694B2

(12) United States Patent
Schmitt et al.

(10) Patent No.: US 8,202,694 B2
(45) Date of Patent: Jun. 19, 2012

(54) COMPOSITION COMPRISING AN OLIGONUCLEOTIDE MIXTURE FOR IMPROVED DETECTION OF HUMAN PAPILLOMAVIRUS GENOTYPES

(75) Inventors: Markus Schmitt, Heidelberg (DE); Tim Waterboer, Mannheim (DE); Michael Pawlita, Eschelbronn (DE)

(73) Assignee: DKFZ Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 66 days.

(21) Appl. No.: 12/675,355

(22) PCT Filed: Aug. 26, 2008

(86) PCT No.: PCT/EP2008/061156
§ 371 (c)(1),
(2), (4) Date: Jun. 2, 2010

(87) PCT Pub. No.: WO2009/027403
PCT Pub. Date: Mar. 5, 2009

(65) Prior Publication Data
US 2011/0027778 A1 Feb. 3, 2011

(30) Foreign Application Priority Data
Aug. 28, 2007 (EP) .................................... 07115138

(51) Int. Cl.
*C12Q 1/68* (2006.01)
*C12P 19/34* (2006.01)
*C07H 21/04* (2006.01)
(52) U.S. Cl. .................... 435/6.12; 435/91.2; 536/24.33; 536/22.1
(58) Field of Classification Search ................. 435/6.12, 435/91.2; 536/24.33; 526/22.1
See application file for complete search history.

(56) References Cited

U.S. PATENT DOCUMENTS 5,527,898 A * 6/1996 Bauer et al. .................. 536/24.3
2007/0031826 A1 2/2007 Lee et al.

FOREIGN PATENT DOCUMENTS

| WO | WO 91/10675 | 7/1991 |
| WO | WO 95/22626 | 8/1995 |
| WO | WO 03/027323 A1 | 4/2003 |

OTHER PUBLICATIONS

Lowe et al. (Nucleic Acid Research, 1990, vol. 18(7), gp. 1757-1761).*
Nucleac acid sequences search reports Accession No. AAT00953, AAT00954, AAT44721, A46158, AAT44704, AAT44697, A46160, AAT00960, AAT44712, AAT44717.*
International Search Report for International Patent Application No. PCT/EP2008/061156 completed Nov. 21, 2008.

Written Opinion of the International Searching Authority for International Patent Application No. PCT/EP2008/061156 completed Nov. 21, 2008.
International Preliminary Report on Patentability for International Patent Application No. PCT/EP2008/061156 completed Aug. 20, 2009.
Parkin, DM et al., "Cancer Burden in the Year 2000, The Global Picture," *Eur. J. Cancer* 37 (Suppl. 8), pp. 4-66 (2001).
de Villiers, E.M., et al., "Classification of papillomaviruses," *Virology*, 324, pp. 17-27 (2004).
Hazard K, et al., "Human papillomavirus subtypes are not uncommon," *Virology*, 362(1), pp. 6-9 (2007).
Munoz et al., Epidemiologic Classification of Human Papillomavirus Types Associated with Cervical Cancer, *N. Engl. J. Med.* 348, pp. 518-527 (2003).
Bosch, et al., "Prevalence of human papillomavirus in cervical cancer: a worldwide perspective," International biological study on cervical cancer (IBSCC) Study Group, *J. Natl. Cancer Inst.*, 87, pp. 796-802 (1995).
Bosch, et al., "The causal relation between human paillomavirus and cervical cancer," *J. Clin. Pathol.*, 55, pp. 244-65 (2002).
Nobbenhuis, et al., "Relation of human papillomavirus status to cervical lesions and consequences for cervical-cancer screening: a prospective study," *Lancet* 354, pp. 20-25 (1999).
Birner et al., "Signal-Amplified Colorimetric In Situ Hybridization for Assessment of Human Papillomavirus Infection in Cervical Lesions," *Mod. Pathol.* 14, pp. 702-709 (2001).
Jacobs, et al., "Distribution of 37 mucosotropic HPV types in women with cytologically normal cervical smears: the age-related patterns for high-risk and low-risk types," *Int. J. Cancer* 87, pp. 221-7 (2000).
de Roda Husman, et al., "The use of general primers GP5 and GP6 elongated at their 3' ends with adjacent highly conserved sequences improves human papillomavirus detection by PCR," *J. Gen. Virol.* 76 (Pt 4), pp. 1057-1062 (1995).
Qu, et al., "PCR detection of human papillomavirus: comparison between MY09/MY11 and GP5+/GP6+ primer systems," *J. Clin. Microbiol.* 35, pp. 1304-1310 (1997).
Baay, M.F., et al., "Comprehensive study of several general and type-specific primer pairs for detection of human papillomavirus DNA by PCR in paraffin-embedded cervical carcinomas," *J. Clin. Microbiol.*, 34, pp. 745-747 (1996).
Kleter, B., et al., "Development and clinical evaluation of a highly sensitive PCR-reverse hybridization line probe assay for detection and identification of anogenital human papillomavirus," *J. Clin. Microbiol.*, 37, pp. 2508-2517 (1999).
Chan, et al., "Biases in human papillomavirus genotype prevalence assessment associated with commonly used consensus primers," *Int. J. Cancer.*, 118, pp. 243-245 (2006).
Gravit, et al., "Improved amplification of genital human paillomaviruses," J. Clin. Microbiol., 38, pp. 357-61 (2000).
Lefevre et al., Canadian Women's HIV Study Group, "Prevalence of selective inhibition of HPV-16 DNA amplification in cervicocaginal lavages," *J. Med. Virol.*, 72(1), pp. 132-137 (2004).
Bezold et al., "Detection of herpes simplex virus and varicella-zoster virus in clinical swabs: frequent inhibition of PCR as determined by internal controls," *Mol. Diagn.* 5(4), pp. 279-284 (2000).

(Continued)

*Primary Examiner* — Kenneth R. Horlick
*Assistant Examiner* — Joyce Tung
(74) *Attorney, Agent, or Firm* — Foley & Lardner LLP

(57) ABSTRACT

The present invention relates to a composition comprising an oligonucleotide mixture. Moreover, the present invention relates to the use of said oligonucleotide mixture for diagnosing different HPV genotypes in a sample of a subject. Further encompassed is a method for diagnosing different HPV genotypes in a sample of a subject and a kit carrying out said method.

7 Claims, 4 Drawing Sheets

OTHER PUBLICATIONS

Figure 1:
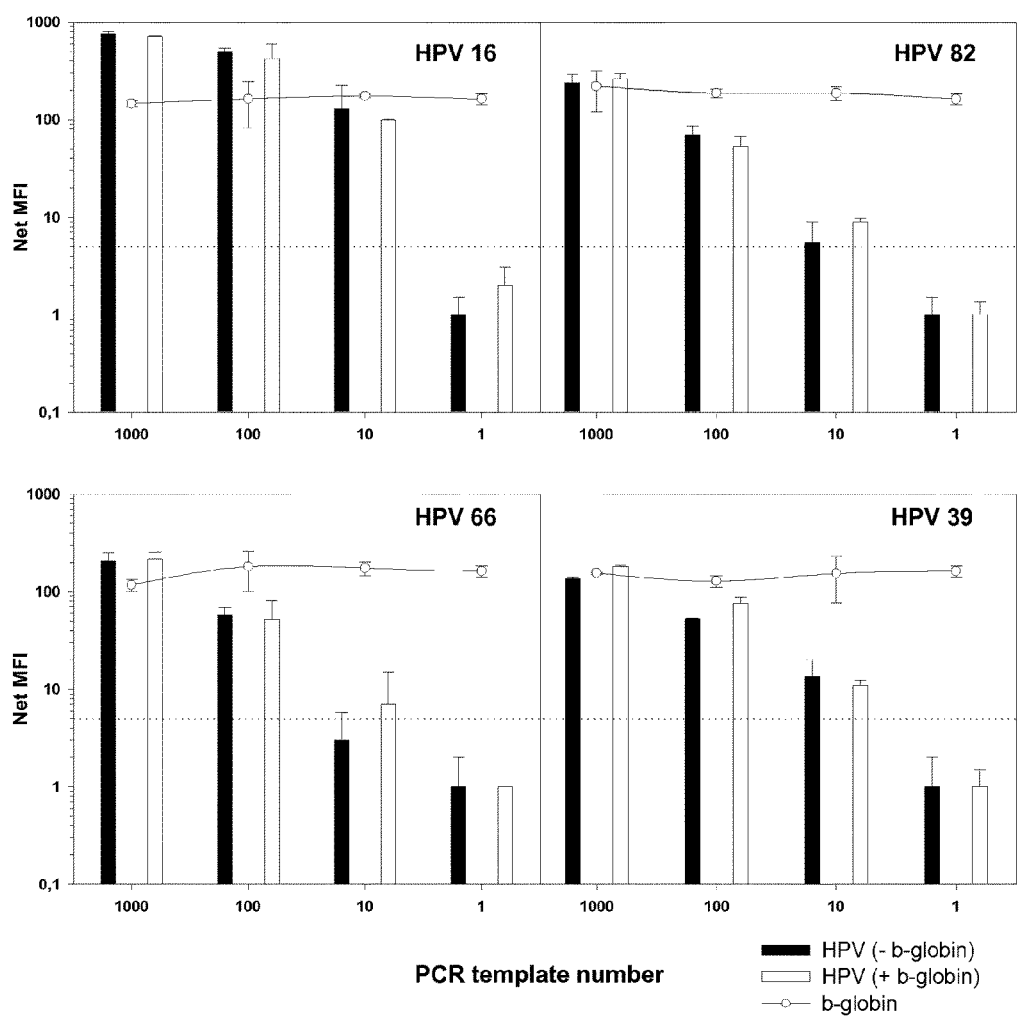

Snijders, et al., "Determination of viral load thresholds in cervical scrapings to rule out CIN 3 in HPV 16, 18, 31 and 33-positive women with normal cytology," *In J. Cancer* 119, pp. 1102-1107 (2006).

Schmitt et al., "Bead-Based Multiplex Genotyping of Human Papillomaviruses," *J. Clin. Microbiol.* 44(2), pp. 504-512 (2006).

van den Brule et al., "GP5+/6+ PCR followed by reverse line blot analysis enables rapid and high-throughput identification of human papillomavirus genotypes," J. Clin. Microbiol., 40, pp. 779-787 (2002).

Melchers et al., "Prevalence of genital HPV infections in a regularly screened population in The Netherlands in relation to cervical cytology," *J. Med. Virol.*, 25, pp. 11-16 (1988).

Melchers et al., "Optimization of human papillomavirus genotype detection in cervical scrapes by a modified filter in situ hybridization test," J. Clin. Microbiol., 27, pp. 106-110 (1989).

Notredame, et al., "T-Coffee: A novel method for fast and accurate multiple sequence alignment," *J. Mol. Biol.*, 302, pp. 205-217 (2000).

Rozen et al., "Primer3 on the WWW for general users and for biologist programmers," *Methods Mol, Biol.*, 132, pp. 365-386 (2000).

Snijders, et al., "HPV DNA detection and typing in cervical scrapes," *Methods Mol. Med.*, 119, pp. 101-114, (2005).

Jeney et al., "Detection and typing of 46 genital human genital human papillomaviruses by the L1F/L1R primer system based multiplex PCR and hybridization" *Journ. of Virol. Methods*, vol. 140, No. 1-2, pp. 32-42 (2007).

Schmitt et al., "Bead-based multiplex genotyping of human papillomaviruses," *Journ. of Clin. Microbiology*, vol. 44, No. 2, pp. 504-512 (2006).

Jiang et al., "Genotyping of human papillomavirus in cervical lesions by L1 consensus PCR and the Luminex xMAP system," *Journ. of Medical Microbiology*, vol. 55, No. 6, pp. 715-720 (2006).

\* cited by examiner

COMPOSITION COMPRISING AN OLIGONUCLEOTIDE MIXTURE FOR IMPROVED DETECTION OF HUMAN PAPILLOMAVIRUS GENOTYPES

CROSS-REFERENCE TO RELATED APPLICATIONS

This application is the National Phase of International Patent Application No. PCT/EP2008/061156, filed on Aug. 26, 2008, which claims the benefit and priority of European Patent Application No. 07115138.5, filed on Aug. 28, 2007. The foregoing applications are incorporated herein by reference in their entirety.

The present invention relates to a composition comprising an oligonucleotide mixture. Moreover, the present invention relates to the use of said oligonucleotide mixture for diagnosing different HPV genotypes in a sample of a subject. Further encompassed is a method for diagnosing different HPV genotypes in a sample of a subject and a kit carrying out said method.

Cervical cancer (cancer of the uterine cervix) is the second most common cancer among women worldwide with about 470,000 newly diagnosed cases and almost 250,000 deaths every year (Parkin, D M et al. 2001. Eur. J. Cancer 37 (Suppl. 8):4-66). The predominant cause for cervical cancer is infection of the cervix with human papillomavirus (HPV), particularly with high-risk HPV genotypes. Human papillomaviruses form a large group of viruses and are small, non-enveloped DNA viruses that infect almost exclusively skin and mucosal cells. To date, the genome of almost 100 various genotypes of human papillomaviruses has been characterized (de Villiers, E. M., C. Fauquet, T. R. Broker, H. U. Bernard, and H. zur Hausen. 2004. Classification of papillomaviruses. Virology 324:17-27), and a much larger number of human papillomaviruses is thought to exist (Hazard K, Andersson K, Dillner J, Forslund O. Human papillomavirus subtypes are not uncommon. Virology. 2007 May 25; 362(1):6-9).

Approximately 50 HPV genotypes are known to infect the mucosa. These mucosal genotypes are classified into three different groups based on their epidemiological association with cancer: "low-risk" human papillomaviruses (LR-HPV), "high-risk" human papillomaviruses (HR-HPV) and "putative high-risk" human papillomaviruses (pHR-HPV). Low-risk human papillomaviruses (including, e.g., HPV genotypes 6, 11, 40, 42, 43, 44 and 70) are primarily found in genital warts and low-grade cervical lesions. Putative high-risk human papillomaviruses, comprising of HPV 26, 53, 66 have not consistently been found in cervical cancer. High-risk human papillomaviruses are associated with the risk of developing cancer (Munoz et al. 2003. N. Engl. J. Med. 348:518-527) and include HPV 16, 18, 31, 33, 35, 39, 45, 51, 52, 56, 58, 59, 68, 73 and 82. HPV 16 and 18 are considered the clinically most relevant ones, as these genotypes are found in almost 70% of cervical cancer patients.

Infection with a high-risk HPV genotype does not necessarily lead to cervical cancer. However, several studies clearly have shown that women infected with high-risk HPV are at substantially higher risk of developing cancer than uninfected women or women being infected with low-risk HPV (Bosch, F. X., M. M. Manos, N. Munoz, M. Sherman, A. M. Jansen, J. Peto, M. H. Schiffman, V. Moreno, R. Kurman, and K. V. Shah. 1995. Prevalence of human papillomavirus in cervical cancer: a worldwide perspective. International biological study on cervical cancer (IBSCC) Study Group. J Natl Cancer Inst 87:796-802.; Bosch, F. X., A. Lorincz, N. Munoz, C. J. Meijer, and K. V. Shah. 2002. The causal relation between human papillomavirus and cervical cancer. J Clin Pathol 55:244-65). In addition, follow-up studies of women with and without cervical abnormalities have indicated that persistence of high-risk HPV infection is a significant risk factor and necessary for the development, maintenance and progression of cervical intraepithelial neoplasia (CIN) (Nobbenhuis, M. A., J. M. Walboomers, T. J. Helmerhorst, L. Rozendaal, A. J. Remmink, E. K. Risse, H. C. van der Linden, F. J. Voorhorst, P. Kenemans, and C. J. Meijer. 1999. Relation of human papillomavirus status to cervical lesions and consequences for cervical-cancer screening: a prospective study. Lancet 354:20-5).

Generally, the progression from HPV infection to cancer is very slow and may take years. However, a crucial step for a successful prevention of cervical cancer is the early detection of an infection with a high-risk HPV genotype. The introduction of the Papanicolaou test, frequently also referred to as Pap test or Pap smear, for cervical cancer screening led to a substantial decrease of mortality caused by cervical cancer in most industrialized countries. For the Papanicolaou test, samples are obtained from the cervix and screened by light microscopy for changes in cell morphology indicating malignant or premalignant cells. Then, samples are classified depending on the severity of the observed lesions. However, diagnosis by cervical cytology is a subjective method, and the quality depends on the standards of the laboratory that provides the service. In fact, sensitivity of cytology was shown to vary between 30 and 90% in different studies (compared to colposcopy and histology as gold standard). This is in marked contrast to the diagnosis by detection of HPV DNA (sensitivity>90% in all studies, average 96%) where commercial kits and standardized protocols were used. Moreover, specific HPV genotypes or even multiple infections with various HPV genotypes can not be identified. The identification of specific HPV genotypes, however, is important, as various HPV genotypes may pose different risks to the affected patients.

Therefore, new test systems were developed in order to allow the identification of specific HPV genotypes. These new test systems are almost exclusively based on the detection of viral, molecular and biochemical markers, such as HPV DNA and RNA.

The FDA-approved Hybrid Capture II Test System (HC2) (Digene Corp., USA) is considered the gold standard for HPV DNA testing in clinical practice. Although this system is reliable, sensitive and easy to handle, it has several disadvantages: a) no genotyping is performed, instead HPV infection is solely attributed to a "low-risk" or "high-risk" group, b) multiple infections can not be identified, and c) it is less sensitive for HPV detection than PCR-based methods. (Birner et al. 2001. Mod. Pathol. 14:702-709).

Several PCR-based methods were developed within the last years, allowing a more precise detection of HPV infection. The majority of these PCR systems use consensus or general primers that bind to highly conserved regions of the HPV genome, e.g. in the L1 region. The amplified PCR products are then subjected to further analysis (e.g. sequencing, restriction fragment length polymorphism (RFLP) analysis or hybridization) in order to identify specific mucosal HPV genotypes.

WO 95/22626 describes the use of two primers, GP5+ and GP6+, for the detection and identification of different HPV genotypes. In comparison to GP5 and GP6 (WO 91/10675), GP5+ and GP6+ primers possess elongated 3' ends improving human papillomavirus detection by PCR (Jacobs, M. V., J. M. Walboomers, P. J. Snijders, F. J. Voorhorst, R. H Verheijen, N. Fransen-Daalmeijer, and C. J. Meijer. 2000. Distribution of 37 mucosotropic HPV types in women with cytologically normal cervical smears: the age-related patterns for high-risk and low-risk types. Int J Cancer 87:221-7). These primers are directed to conserved sequence regions within the L1 region of the HPV genome. However, the HPV sequence to which the primers are directed is not 100% conserved. Recent data showed differences in the ability to amplify mucosal HPV genotypes depending on the number and position of mismatches between primer and target sequence of specific genotypes (de Roda Husman, A. M., J. M. Walboomers, A. J. van den Brule, C. J. Meijer, and P. J. Snijders. 1995. The use of general primers GP5 and GP6 elongated at their 3' ends with adjacent highly conserved sequences improves human papillomavirus detection by PCR. J Gen Virol 76 (Pt 4):1057-62; Qu, W., G. Jiang, Y. Cruz, C. J. Chang, G. Y. Ho, R. S. Klein, and R. D. Burk. 1997. PCR detection of human papillomavirus: comparison between MY09/MY11 and GP5+/GP6+ primer systems. J Clin Microbiol 35:1304-10). Thus, the caused selective over- and under-amplification, respectively, may not reflect the real distribution of HPV genotypes. As a result, this may lead to an incorrect assessment of the prevalence of poorly detectable genotypes in cervical specimens (Baay, M. F., W. G. Quint, J. Koudstaal, H. Hollema, J. M. Duk, M. P. Burger, E. Stolz, and P. Herbrink. 1996. Comprehensive study of several general and type-specific primer pairs for detection of human papillomavirus DNA by PCR in paraffin-embedded cervical carcinomas. J Clin Microbiol 34:745-7). Moreover, the use of the GP5+/GP6+ PCR may lead to false-negative results when diagnosing certain HPV genotypes (Kleter, B., L. J. van Doom, L. Schrauwen, A. Molijn, S. Sastrowijoto, J. ter Schegget, J. Lindeman, B. ter Harmsel, M. Burger, and W. Quint. 1999. Development and clinical evaluation of a highly sensitive PCR-reverse hybridization line probe assay for detection and identification of anogenital human papillomavirus. J Clin Microbiol 37:2508-17; Chan, P. K., T. H. Cheung, A. O. Tam, K. W. Lo, S. F. Yim, M. M. Yu, K. F. To, Y. F. Wong, J. L. Cheung, D. P. Chan, M. Hui, and M. Ip. 2006. Biases in human papillomavirus genotype prevalence assessment associated with commonly used consensus primers. Int J Cancer 118:243-5). There is also evidence that the GP5+/GP6+ PCR detects multiple HPV infections to a lower extent than other consensus or broad spectrum PCR (Kleter, B., L. J. van Doom, L. Schrauwen, A. Molijn, S. Sastrowijoto, J. ter Schegget, J. Lindeman, B. ter Harmsel, M. Burger, and W. Quint. 1999. Development and clinical evaluation of a highly sensitive PCR-reverse hybridization line probe assay for detection and identification of anogenital human papillomavirus. J Clin Microbiol 37:2508-17; Qu, W., G. Jiang, Y. Cruz, C. J. Chang, G. Y. Ho, R. S. Klein, and R. D. Burk. 1997. PCR detection of human papillomavirus: comparison between MY09/MY11 and GP5+/GP6+ primer systems. J Clin Microbiol 35:1304-10).

In addition, the control of DNA integrity is an important step in analysis of clinical samples to reduce the number of false-negative results. Conventionally, GP5+/6+ PCR is mostly applied to samples, which had been pre-screened by an external beta-globin (b-globin) PCR with primers, such as BGCO3 and BGCO5, and subsequent analysis of the PCR product by gel electrophoresis (de Roda Husman, A. M., J. M. Walboomers, A. J. van den Brule, C. J. Meijer, and P. J. Snijders. 1995. An internal DNA quality control in the HPV PCR has been already described for the MY09/11 or PGMY09/11 PCR (Gravitt, P. E., C. L. Peyton, T. Q. Alessi, C. M. Wheeler, F. Coutlee, A. Hildesheim, M. H. Schiffman, D. R. Scott, and R. J. Apple. 2000. Improved amplification of genital human papillomaviruses. J Clin Microbiol 38:357-61). However, the authors have described that the used b-globin primers, GH20 and PC04, could decrease the analytic sensitivity for HPV. Nonetheless, an internal DNA quality control, with no concurrent impairment of the HPV amplification sensitivity, would be desirable for several reasons: In addition to gain of time and reduction of costs, an internal DNA quality control could also explain a failure of the HPV PCR due to mistakes in the PCR preparation.

In contrast to DNA quality controls, integrated PCR controls that comprise an exogenous control polynucleotide (internal PCR control, IC) can screen for PCR failure due to inhibitors present in the sample or due to mistakes in the PCR preparation. A recent study has demonstrated that 8% of crude cervical DNA samples contained inhibitors for quantitative HPV 16 amplification (Lefevre J, Hankins C, Pourreaux K, Voyer H, Coutlee F; Canadian Women's HIV Study Group. Prevalence of selective inhibition of HPV-16 DNA amplification in cervicovaginal lavages. J Med Virol. 2004 January; 72(1):132-7.). Another study has demonstrated that distinct primer pairs were not influenced equally by PCR inhibitors (Bezold et al., Detection of herpes simplex virus and varicella-zoster virus in clinical swabs: frequent inhibition of PCR as determined by internal controls, Mol Diagn. 2000 December; 5(4):279-84.). As a consequence, screening for inhibitors of the HPV PCR is essential.

Thus, the technical problem underlying the present invention may be seen as the provision of means and methods for efficiently and reliably detecting and diagnosing different human papillomavirus (HPV) genotypes and, in particular, the high-risk and putative high-risk genotypes without the drawbacks as referred to above. The technical problem is solved by the embodiments characterized in the claims and herein below.

Accordingly, the present invention relates to a composition comprising an oligonucleotide mixture, wherein said oligonucleotide mixture comprises (a) oligonucleotides having a nucleic acid sequence as shown in SEQ ID NOs: 1, 2, 3, 4, 5, 6, 7, 8, 9, 10, 11, and 12, or (b) oligonucleotides which are capable of specifically amplifying polynucleotides which are amplified by the oligonucleotides of (a).

The term "oligonucleotide mixture" as meant herein relates to a mixture of different oligonucleotide molecular species. In addition, the mixture may comprise further components other than the oligonucleotides, e.g. components for the amplification of polynucleotides of mucosal HPV genotypes, preferably by polymerase chain reaction (PCR). Such components may be, but are not limited to, an aqueous buffer, a water soluble magnesium salt, deoxythymidine triphosphate (dTTP), deoxyadenosine triphosphate (dATP), deoxycitidine triphosphate (dCTP) and deoxyguanosine triphosphate, (dGTP) and a DNA polymerase, e.g. the thermostable DNA polymerase from Thermus aquaticus.

The term "oligonucleotide" as used herein relates to an oligonucleotide molecular species wherein all molecules of the molecular species have a specific nucleic acid sequence. Preferably, the term "oligonucleotide" relates to a primer for DNA amplification techniques such as PCR. An oligonucleotide shall comprise a number of nucleotides being sufficient for specific binding to a sequence stretch of a target polynucleotide. Preferably, an oligonucleotide as meant herein has between 15 and 30 nucleotides in length, more preferably between 18 and 28 nucleotides in length, and most preferably between 23-25 nucleotides in length. Preferably, the sequence of the oligonucleotide is not degenerated. Preferably, the oligonucleotide is a single-stranded oligodesoxyribonucleotide. However, due to self-complementarity the oligonucleotide may be partially double-stranded under certain conditions (depending on, e.g., the sequence of the oligonucleotide, the salt concentration and the temperature). Particularly preferred oligonucleotides have the specific sequences and/or properties referred to above.

The oligonucleotides of the present invention, preferably, are used as a starting molecule for the synthesis of a polynucleotide which is sufficiently complementary to the nucleic acid strand to be copied by an appropriate amplification technique, preferably by PCR, for polynucleotides. The oligonucleotide mixture of the present invention shall contain at least one forward and at least one backward oligonucleotide. Forward and backward oligonucleotides are frequently also referred to as forward and reverse oligonucleotides, or as 5' and 3' oligonucleotides. It is to be understood that the synthesized polynucleotides may not be 100% complementary to the copied target sequence, e.g due to mismatches between the oligonucleotide sequence and the sequence stretch of a target polynucleotide.

Preferably, an oligonucleotide according to the invention targets one of the two specific L1 consensus regions of HPV genome. These specific regions are highly (but not 100%) conserved between the various known mucosal HPV genotypes and are disclosed in, e.g., in WO 95/22626, which hereby is incorporated by reference in its entirety. It is well known in the art that the GP5+ oligonucleotide (sequence as shown in SEQ ID NO: 1) and the GP6+ oligonucleotide (sequence as shown in SEQ ID NO: 2) target these regions. An alignment of mucosal HPV with the GP5+ and GP6+ oligonucleotides in WO 95/22626 can be found in Table 1 (Example 1). In order to target one of the conserved two L1 regions of the various human papillomaviruses as referred to above, an oligonucleotide of the invention shall be complementary to said region. However, it is to be understood that it is not necessary that said oligonucleotide is 100% complementary to said region, i.e. some mismatches may occur. The ability of an oligonucleotide to hybridize to a target sequence may be assessed by the Tm (melting temperature). The Tm is the temperature at which 50% of double-stranded nucleic acid strands are dissociated into single strands. In addition to the sequence, the Tm also depends on the environmental conditions (e.g. salt concentration) and may be determined empirically or estimated by using suitable computer software (Le Novère, MELTING, computing the melting temperature of nucleic acid duplex. Bioinformatics. 2001 December; 17(12): 1226-7). Generally, the higher the Tm, the more stable is a double stranded structure.

The oligonucleotides of the present invention may be labelled or contain other modifications which allow a detection and/or analysis of an amplification product and/or the binding to a carrier. Labelling can be done by various techniques well known in the art and depending of the label to be used. Particularly, the oligonucleotides may be biotinylated in order to enable the binding of the amplification products to a streptavidin surface or fluorescent conjugate. Moreover, labels to be used in the context of the present invention may be, but are not limited to, fluorescent labels comprising, inter alia, fluorochromes such as R-phycoerythrin, Cy3, Cy5, fluorescein, rhodamin, Alexa, or Texas Red. However, the label may also be an enzyme or an antibody. It is envisaged that an enzyme to be used as a label will generate a detectable signal by reacting with a substrate. Suitable enzymes, substrates and techniques are well known in the art. An antibody to be used as label may specifically recognize a target molecule which can be detected directly (e.g., a target molecule which is itself fluorescent) or indirectly (e.g., a target molecule which generates a detectable signal, such as an enzyme). The oligonucleotides of the present invention may also contain 5' restriction sites, locked nucleic acid molecules (LNA) or be part of a peptide nucleotide acid molecule (PNA). Such PNA can be, in principle, detected via the peptide part by, e. g., antibodies.

Preferably, an oligonucleotide mixture of the present invention shall comprise oligonucleotides having a nucleic acid sequence shown in SEQ ID NOs: 1, 2, 3, 4, 5, 6, 7, 8, 9, 10, 11, and 12.

Moreover, the present invention also relates to a composition comprising an oligonucleotide mixture, wherein said oligonucleotide mixture comprises oligonucleotides which are capable of specifically amplifying polynucleotides which are amplified by the oligonucleotides having a nucleic acid sequence as shown in SEQ ID NOs: 1, 2, 3, 4, 5, 6, 7, 8, 9, 10, 11, and 12. It is to be understood that the oligonucleotide mixture comprises backward and forward oligonucleotides, preferably more than one backward oligonucleotide and more than one forward oligonucleotide, more preferably three backward oligonucleotides and nine forward oligonucleotides. The sequences of the oligonucleotides contained in the oligonucleotide mixture can be determined by comparing/aligning the two conserved sequences of the L1 region of the mucosal human papillomaviruses to be detected (Table 1, see Examples). After alignment, the sequence of the oligonucleotides may be determined by the following criteria: 1) in one oligonucleotide up to three mismatches with regard to the conserved sequence of any of the HPV genotype to be detected, thus either no mismatch, one mismatch, two mismatches, or three mismatches, wherein, preferably, the mismatches are close to the 5' end of the oligonucleotide, and wherein an oligonucleotide with three mismatches has at least 5 perfect matching nucleotides between the 3' end of said oligonucleotide and the mismatch which is closest to the 3' end of the respective oligonucleotide, or 2) in a corresponding oligonucleotide pair, i.e. in forward and backward oligonucleotides, up to five mismatches, thus either no mismatch, one mismatch, two mismatches, three mismatches, four mismatches, or five mismatches (e.g., if there are four mismatches in the forward primer, the number of mismatches in the corresponding backward primer must not exceed one mismatch), wherein an oligonucleotide with four mismatches has at least eight perfect matching nucleotides between the 3' end of said oligonucleotide and the mismatch which is closest to the 3' end of the respective oligonucleotide.

Also encompassed by the present invention are compositions comprising an oligonucleotide mixture wherein the oligonucleotides have a nucleic acid sequence as shown in SEQ ID NOs: 1, 2, 3, 4, 5, 6, 7, 8, 9, 10, 11, and 12, and wherein one or more, preferably two, three, four, five, six, seven, eight, nine of said oligonucleotides have been deleted, substituted and/or added. The sequence of an oligonucleotide that may be added to a composition of the invention and/or that may replace any one of the oligonucleotides of the invention (having a nucleic acid sequence as shown in SEQ ID NOs: 1, 2, 3, 4, 5, 6, 7, 8, 9, 10, 11, and 12) preferably, may be determined by applying the criteria as defined above. Accordingly, said oligonucleotide may have a nucleic acid sequence as shown in SEQ ID NOs: 16, 17, 18, 19, 20, 21 or 22. Thus, a composition according to the invention may also comprise an oligonucleotide mixture, wherein said oligonucleotide mixture comprises (a) oligonucleotides having a nucleic acid sequence as shown in SEQ ID NO: 1, 2, 3, 4, 5, 6, 7, 8, 9, 10, 11, 12, 16, 17, 18, 19, 20, 21 and 22 or (b) oligonucleotides which are capable of specifically amplifying polynucleotides which are amplified by the oligonucleotides of (a).

The amount and/or the concentration of the oligonucleotides of the invention in an oligonucleotide mixture may be any amount or concentration deemed appropriate. The oligonucleotide mixture may comprise different numbers of forward oligonucleotides and backward oligonucleotides (for a list of forward and backward oligonucleotides which may be used in the embodiments of the present invention, please see Example 1). E.g., the oligonucleotide mixture may comprise three forward oligonucleotides and nine backward oligonucleotides for the amplification of HPV DNA or RNA. Therefore, the amounts and/or concentrations of the individual oligonucleotides of the invention may differ and, thus, a solution comprising said oligonucleotides may not be equimolar with respect to the oligonucleotides. Preferred concentrations of the oligonucleotides in a solution suitable for the amplification of polynucleotides can be found in the Examples. A particularly preferred concentration of each forward oligonucleotide is 0.2 µM and 0.4 µM for each backward oligonucleotide. Moreover, it is to be understood that the person skilled in the art is able to adjust the concentrations of the oligonucleotides of the invention in order to optimize the amplification of HPV specific polynucleotides and, thus, to optimize the sensitivity and specificity of a diagnosis without further ado.

Preferably, the oligonucleotide mixture comprised by the composition of the present invention allows the detection of various mucosal HPV genotypes, particularly, of the high-risk HPV genotypes 16, 18, 31, 33, 35, 39, 45, 51, 52, 56, 58, 59, 68, 73 and 82, putative high-risk HPV types 26, 53 and 66 and low-risk HPV types 6, 11 and 70.

Advantageously, it was found in the studies underlying the present invention that a composition comprising an oligonucleotide mixture, wherein said oligonucleotide mixture comprises (a) oligonucleotides having a nucleic acid sequence as shown in SEQ ID NOs: 1, 2, 3, 4, 5, 6, 7, 8, 9, 10, 11, and 12, or (b) oligonucleotides which are capable of specifically amplifying polynucleotides which are amplified by the oligonucleotides of (a), is required for sufficient detection, and therefore for diagnosing the mucosal HPV genotypes in a sample of a subject. Specifically, it was shown that the use of a composition comprising an oligonucleotide mixture, wherein said oligonucleotide mixture comprises oligonucleotides having a nucleic acid sequence as shown in SEQ ID NOs: 1, 2, 3, 4, 5, 6, 7, 8, 9, 10, 11, and 12 (i.e. oligonucleotides that are directed to relatively conserved sequences in the L1 region of the HPV genome) is more reliable than prior art as a large number of mucosal HPV genotypes can be simultaneously detected in a sample with a higher sensitivity than in prior art (see Examples). In the studies underlying the present invention HPV types 6, 11, 16, 18, 26, 30, 31, 33, 35, 39, 42, 43, 44, 45, 51, 52, 53, 56, 58, 59, 66, 67, 68 (subtypes A and B), 69, 70, 73, 82 (including IS39 and MM4) were detected. When using the composition of the present invention, it was even possible to reproducibly detect HPV genotypes that are known to be poorly-detectable by the GP5+/GP6+ HPV detection system, such as HPV 30, 39, 42, 44, 51, 52, 53, 68, 73, and 82. It has to be understood that also additional HPV genotypes (other than the tested genotypes) may be detected when using said composition. Moreover, an exogenous control polynucleotide, (that allows screening for HPV PCR inhibitors), as well as oligonucleotides for the amplification of an endogenous control polynucleotide, e.g., DNA comprised already by the samples, were included in the composition of the present invention. Surprisingly, the use of an exogenous control polynucleotide and oligonucleotides for the amplification of an endogenous polynucleotide did not significantly affect the detection of HPV genotypes. This is particularly beneficial for the simultaneous monitoring of HPV infection and DNA quality and may prevent false-negative results. In comparison to a conventional external DNA quality control, these approaches are less time- and cost-intensive, allow screening for PCR inhibitors, and thereby monitor a failure of the HPV PCR. Prior art does not teach the efficient simultaneous amplification (in a single tube) of mucosal HPV genotypes and of an exogenous control polynucleotide and of an endogenous control nucleotide when using the GP5+/GP6+ oligonucleotides. Thus the compositions and the methods according to the present invention will be, if applied, very beneficial to the health system, as they allow an early, more reliable and cost effective diagnosis of single as well as multiple infections with different HPV genotypes, particularly with high risk genotypes.

Viral load of HPV is considered to play an important role in the development of cervical cancer (Snijders, P. J., C. J. Hogewoning, A. T. Hesselink, J. Berkhof, F. J. Voorhorst, M. C. Bleeker, and C. J. Meijer. 2006. Determination of viral load thresholds in cervical scrapings to rule out CIN 3 in HPV 16, 18, 31 and 33-positive women with normal cytology. Int J Cancer 119:1102-7). Advantageously, the composition of the present invention not only allows for detection of various HPV genotypes as described herein, the composition also allows for determination for the viral load of various HPV genotypes in a sample. Specifically, the amplification products that were amplified by using the composition of the present invention were quantified by assessing the intensity of various hybridization signals. It was shown that the intensity of the observed hybridization signals correlates with the severity of HPV infection, and therefore with the viral load. For example, the median intensity of the hybridization signal for samples graded HSIL (high-grade squamous intraepithelial lesions), i.e. a more severe form of HPV infection, was approximately tenfold the median intensity of samples graded NILM (no intraepithelial lesions; a mild form of HPV infection, see Examples, as well as FIG. 3 and FIG. 4). Thus, the composition of the present invention also allows for differentiating between mild and severe forms of HPV infection, and, therefore to assess the severity of HPV infection. The sensitivity and specificity of the diagnosis can be even more enhanced when the composition of the present invention further comprises oligonucleotides for the amplification of an endogenous control polynucleotide (for an explanation of the term endogenous control, see below). Particularly, oligonucleotides were included in the composition that specifically amplify the human beta globin gene (the sequence of the oligonucleotides is shown in SEQ ID NO: 13 and SEQ ID NO: 14). It was shown that the amplification of the endogenous control gene is suppressed in samples with a high viral load (indicating a more severe form of HPV infection). Therefore, in samples with large amounts of viral DNA, hybridization signals of increased intensity were observed for HPV (compared with the hybridization signal of sample with a low viral load), whereas the intensity of the hybridization signal for the endogenous control was reduced (compared with the hybridization signal of samples with a low viral load). Thus, by calculating the ratio of the amount of amplified HPV polynucleotides to the amount of the amplified product for the endogenous control DNA, the severity of a infection with various HPV genotypes, preferably, high risk HPV genotypes can be determined.

The composition of the present invention, preferably, further comprises oligonucleotides for the amplification of an endogenous control polynucleotide sequence.

The term "oligonucleotides for the amplification of an endogenous control polynucleotide sequence" as meant herein relates to oligonucleotides that specifically amplify an endogenous control polynucleotide sequence comprised by the sample. The person skilled in the art knows that such oligonucleotides can be included as a positive control in a PCR reaction mix in order to assess, e.g., the quality of the template nucleic acids and, thus, of a sample. The term "sample" is specified elsewhere in this application. Moreover, errors that occurred when setting up the PCR reaction maybe assessed by using oligonucleotides that specifically amplify an endogenous control polynucleotide sequence. Efficient amplification of an endogenous control polynucleotide, preferably, indicates that an amplification reaction was successful and the DNA of sufficient quality, whereas inefficient amplification, preferably, indicates that an amplification reaction was not successful due to an inappropriate sample or errors in the PCR setup. In the latter cases, a PCR reaction may have to be repeated, e.g., with a freshly obtained sample and/or freshly purified DNA or RNA. Thus, the use of oligonucleotides that specifically amplify an endogenous control polynucleotide sequence may prevent false-negative results.

Preferably, the oligonucleotides that specifically amplify an endogenous control polynucleotide sequence amplify at least one human polynucleotide sequence because the sample to be analyzed in the context of the present invention is a sample obtained from a human (see below). Endogenous control polynucleotide sequences are sequences or sequence stretches of endogenous polynucleotides already present in the sample of the subject. Endogenous control polynucleotide sequences are, preferably, polynucleotide sequences of genes selected from the group consisting of β-globin, GAPDH, Actin and Ubiquitin C. The endogenous control polynucleotides may be "one copy" polynucleotides of the human genome, i.e. a sequence which is present in the haploid human genome only once, or the oligonucleotides may also be directed to multicopy regions. Examples for suitable oligonucleotides for the amplification of endogenous control polynucleotide sequence are oligonucleotides that allow the amplification of part of the human β-globin nucleic acid sequence, e.g. by PCR. Preferably, the amplified polynucleotide endogenous control sequence is not significantly shorter or longer than the amplified polynucleotide sequences of the L1 region of various HPV genotypes as referred to above, more preferably the amplified polynucleotide endogenous control sequence has a length of 150 to 300 bp, most preferably of 180 to 220 bp. It is to be understood that the use of oligonucleotides for the amplification of an endogenous control polynucleotide sequence, preferably, does not significantly affect the efficiency of the amplification of other PCR amplifications carried out in the same assay (e.g., in the same tube or container), e.g., the formation of primer-dimers and of hairpin structures in the primers should be avoided. The skilled person knows how to determine whether the use of oligonucleotides for the amplification of a endogenous control polynucleotide significantly affects the amplification efficiency of the amplification of polynucleotides carried out in the same assay (e.g. by carrying out amplification reactions using a composition according to the invention either with oligonucleotides for the amplification of an endogenous control polynucleotide sequence or without said oligonucleotides, and by quantifying the thus obtained amplification products).

Most preferably, oligonucleotides for the amplification of an endogenous control polynucleotide sequence have a nucleic acid sequence as shown in SEQ ID NO: 13 and/or SEQ ID NO: 14.

Moreover, the composition of the present invention, preferably, further comprises an exogenous control polynucleotide.

The term "exogenous control polynucleotide" as used herein relates to a polynucleotide that is not naturally occurring in a sample of a subject and, thus, that is foreign to said sample. The term "sample" is specified elsewhere in this application (see below). The exogenous control polynucleotide is added to and, thus, is comprised by the composition of the present invention and serves as a control for the efficiency of the amplification of HPV specific polynucleotides. Preferably, the exogenous control polynucleotide can be amplified, e.g. simultaneously amplified, by an oligonucleotide mixture according to the present invention (e.g. by oligonucleotides having a nucleic acid sequence as shown in SEQ ID NOs: 1, 2, 3, 4, 5, 6, 7, 8, 9, 10, 11, and 12). Preferably, the nucleic acid sequence of the exogenous control polynucleotide comprises an inner polynucleotide region that is not related to a HPV sequence and two outer polynucleotide regions (one region 5' to the inner polynucleotide region and one region 3' to the inner polynucleotide region) that can be targeted by oligonucleotides having a nucleic acid sequence as shown in SEQ ID NOs: 1, 2, 3, 4, 5, 6, 7, 8, 9, 10, 11, and 12. Said outer regions shall allow the amplification of the exogenous control polynucleotide sequence when using an oligonucleotide mixture of the invention. The inner polynucleotide region, preferably, may have any sequence, provided that it can be distinguished from amplified HPV specific polynucleotides, from amplified endogenous control polynucleotides (i.e. that it does not show significant sequence similarity to amplified HPV and endogenous control polynucleotides that might interfere with the detection of these polynucleotides). The skilled person is able to determine a sequence of said inner polynucleotide region. Preferably, the exogenous control polynucleotide is not significantly shorter or longer than the amplified HPV polynucleotide sequences as referred to in this specification, more preferably the amplified polynucleotide exogenous control sequence has a length of 100 to 180 bp, most preferably of 120 to 160 bp. Preferably, the amplification of the exogenous control polynucleotide does not affect the type-specific detection of HPV genotypes. Preferably, the exogenous control polynucleotide can be detected by use of an oligonucleotide probe that is specific for the exogenous control polynucleotide sequence. More preferably, the exogenous control polynucleotide can be detected by use of an oligonucleotide probe that is specific for inner polynucleotide sequence of the exogenous control polynucleotide sequence and, thus, by use of an oligonucleotide that does not target the outer polynucleotide region (as referred to above), or any sequence of the amplified HPV polynucleotides, or of the endogenous control polynucleotide. The exogenous control polynucleotide may be prepared by any method deemed appropriate, e.g., it may be a synthetic polynucleotide such as a chemically synthesized polynucleotide. Moreover, said exogenous control polynucleotide may be present in a plasmid. A method for preparing an exogenous control polynucleotide is shown in the Examples. The use of an exogenous control polynucleotide is particularly beneficial when PCR inhibitors are present in clinical samples and when errors occur during setting up of the PCR reaction that may lead to otherwise undetected false-negative results. Efficient amplification of an exogenous control polynucleotide, preferably, indicates that an HPV amplification reaction was successful, whereas inefficient amplification, preferably, indicates that an HPV amplification reaction was not successful, e.g. due to inhibiting agents and/or errors in the PCR preparation. Thus, efficient amplification of an exogenous control polynucleotide, more preferably, indicates that results obtained for an amplification reaction using an oligonucleotide mixture of the present invention may allow for a reliable diagnosis of different HPV genotypes. It is to be understood that the exogenous polynucleotide sequence is comprised by the composition of the present invention in an amount that allows an efficient amplification of HPV specific polynucleotides without significantly reducing the sensitivity for diagnosising a present HPV infection. Preferred concentrations of the exogenous control polynucleotide in the composition of the present invention can be determined by the skilled person with any undue experimentation, e.g., by performing amplification reactions with various dilutions of the exogenous control polynucleotide.

Most preferably, the exogenous control polynucleotide has a nucleic acid sequence as shown in SEQ ID NO: 15.

Furthermore, the present invention relates to the use of the composition of the present invention for diagnosing different HPV genotypes in a sample of a subject, wherein the composition further may comprise oligonucleotides for the amplification of an endogenous polynucleotide as DNA quality control and/or an exogenous polynucleotide as internal PCR control.

The term "different HPV genotypes" relates to at least one HPV genotype, e.g. at least two, at least three, at least four, at least five, at least six, at least seven, at least eight, at least nine, at least ten or more genotypes. HPV genotypes that may be diagnosed in the context of the present invention, preferably, are the alpha genus mucosal HPV genotypes 6, 11, 13, 16, 18, 26, 30, 31, 32, 33, 34, 35, 39, 42, 43, 44, 45, 51, 52, 53, 54, 55, 56, 58, 59, 61, 62c, 64, 66, 67, 68 (subtypes A and B), 69, 70, 71 72, 73, 74, 81, 82 (including IS39 and MM4), 83, 84, 85c, 86c, 87c, 89c/Cp6108, 90c, 97, 102 and 106, the alpha genus cutaneous HPV genotypes 2, 3, 7, 10, 27, 28, 29, 40, 57, 77, 91c and 94, more preferably 6, 11, 13, 16, 18, 26, 30, 31, 32, 33, 35, 39, 42, 43, 44, 45, 51, 52, 53, 54, 56, 58, 59, 66, 67, 68 (subtype A and B), 69, 70, 72, 73, 82 (including IS39 and MM4), 89c/Cp6108, and most preferably the putative high-risk HPV genotypes 26, 53, 66 and the high-risk HPV genotypes 16, 18, 31, 33, 35, 39, 45, 51, 52, 56, 58, 59, 68, 73 and 82. Preferably, the different HPV genotypes are diagnosed simultaneously. The diagnosis and/or the determination of different HPV genotypes is done by identifying amplified polynucleotides that are specific for different HPV genotypes and that are obtained by the use of a composition according to the invention (as described elsewhere in the specification). Preferably, the amplification of HPV genotype-specific polynucleotides and/or the determination of different HPV genotypes is carried out simultaneously, more preferably in the same container (thus in the same solution).

Moreover, the present invention relates to a method for diagnosing different HPV genotypes in a sample of a subject comprising the steps of
a) contacting a sample of a subject suspected to comprise different HPV genotypes with the composition of the present invention under conditions which allow for amplification of polynucleotides; and
b) determining the different HPV genotypes based on the amplified polynucleotides obtained in step a).

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring or confirmation of infection with at least one HPV genotype. The method may be carried out manually or assisted by automation. Preferably, step (a) and/or (b) may in total or in part be assisted by automation, e.g., by suitable robotic and sensory equipment for the determination in step (b).

The term "diagnosing" as used herein refers to assessing the probability according to which a subject is suffering or will suffer from a disease, infection or condition referred to in this specification, preferably from an infection with different HPV genotypes. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. Preferably, the probability envisaged by the present invention allows that the diagnosis will be correct for at least 60%, at least 70%, at least 80%, or at least 90% of the subjects of a given cohort or population.

The term "subject" as used herein relates to humans regardless of their age, gender or subpopulation. However, it is envisaged by the present invention that the subject may suffer from an HPV infection as specified elsewhere in this specification. Moreover, the subject referred to in accordance with the present invention is, preferably, a subject suspected to comprise one or more different HPV genotypes, preferably different mucosal HPV genotypes, more preferably different high-risk HPV genotypes, or a subject which has not yet developed symptoms associated with an HPV infection, i.e. a subject which is symptomatically healthy. A subject may be suspected to comprise at least one HPV genotype, e.g., due to a positive Pap test or due to sexual contact with a subject comprising different HPV genotypes. The subject may be a male or female. Preferably, the subject is a female.

The term "comprising a HPV genotype" in this context shall relate to being infected with a HPV genotype.

The term "under conditions which allow for polynucleotide amplification" as used herein is understood by the skilled person. The term polynucleotide amplification relates to a template-dependent process which results in an increase of the amount of a nucleic acid molecule relative to its initial amount. In accordance with the present invention the amplification of a polynucleotide of interest shall allow its detection by any method deemed appropriate and/or, e.g., described herein below. The amplification of a polynucleotide of interest may be carried out by well-known methods, preferably by polymerase chain reaction (PCR), but also by reverse transcriptase PCR, real-time PCR, nucleic-acid sequence based amplification (NASBA), and isothermal amplification methods using polymerases and specific oligonucleotides as primers. PCR methods are well known in the art. Preferred embodiments of a PCR in the context of the present invention are described in the Examples. Moreover, components that are needed for carrying out a PCR are described herein above. The person skilled in the art knows how to optimize a PCR protocol in order to amplify sufficient amounts of the respective amplification product, e.g., by adjusting the dNTP, template, oligonucleotide, or the template concentration, by using different thermostable DNA polymerases, or by adjusting the PCR cycling program (by adjusting, e.g., the annealing temperature, ramping rates). It is to be understood that the amplification by PCR is carried out under conditions which prevent a contamination of a template or any other component of the whole reaction mixture that may cause false-positive results. The term "contamination" in this context is well understood. The person skilled in the art knows how to take measures to prevent a contamination of a sample.

The term "sample" refers to a sample of a body fluid, to a sample of separated cells or to a sample from a tissue or an organ or to a sample of wash/rinse fluid obtained from an outer or inner body surface. The samples comprises polynucleotides, preferably the sample comprises DNA. Samples can be obtained by well known techniques and include, preferably, scrapes or biopsies from the urogenital tract, perianal regions, anal canal, the oral cavity, the upper aerodigestive tract and the epidermis. Such samples can be obtained by use of brushes, (cotton) swabs, spatula, rinse/wash fluids, punch biopsy devices, puncture of cavities with needles or surgical instrumentation. Preferably, the scrapes contain mucosal cells. However, samples of blood, plasma, serum, urine, saliva, lacrimal fluid, stool are also encompassed by the method of the present invention. Tissue or organ samples may be obtained from any tissue or organ by, e.g., biopsy or other surgical procedures. Separated cells may be obtained from the body fluids or the tissues or organs by separating techniques such as filtration, centrifugation or cell sorting. Preferably, cell, tissue or organ samples are obtained from those cells, tissues or organs which are known or suspected targets of alpha genus HPV genotypes, more preferably mucosal HPV genotypes, and, therefore, may comprise HPV-specific polynucleotides. It is to be understood that the sample may be further processed in order to carry out the method of the present invention. Particularly, polynucleotides such as DNA or RNA, preferably DNA, might be extracted and/or purified from the obtained sample by methods and means known in the art (e.g., see Examples). Thus, the term sample also may relate to polynucleotides, preferably DNA, purified and/or extracted from any sample as mentioned to above.

The term "determining the different HPV genotypes based on the amplified polynucleotides" relates to identifying amplified polynucleotides that are specific for the various, individual HPV genotypes (as specified elsewhere in this application). Preferably, this will be achieved by detecting the presence or absence of amplified polynucleotides being specific for the HPV genotypes to be detected. Based on the determination a diagnosis can be made. If an amplified polynucleotide that is specific for an individual HPV genotype is present, then an infection with the respective HPV genotype can be diagnosed. If there is no amplification product for a polynucleotide that is specific for a certain HPV genotype (thus, if an amplified polynucleotide is absent), then "no infection" with the respective HPV genotype can be diagnosed. If one or more than one high-risk HPV genotype is determined in a sample of a subject, said subject is at risk of developing cervical or other HR-HPV-associated cancers, if only low-risk HPV genotypes or no HPV genotypes are detected in a sample of a subject, said subject, preferably, is not at risk of developing cervical or other HR-HPV-associated cancers. Other HR-HPV-associated cancers in this context may be, but are not limited to, oesophageal cancer, oral cancer, pharyngeal cancer, penile cancer, perianal cancer, vulvar cancer, laryngeal cancer, laryngeal verrucous cancer, tonsillar cancer, and vaginal cancer. A suitable treatment may be started according to the diagnosis. The success of a treatment, i.e. removal of the infected or diseased cells or tissues may be monitored by the methods of the present invention.

Determining the different HPV genotypes based on the amplified polynucleotides can be done by any method known in the art and deemed appropriate. The determination is based on the detection and/or identification of individual, amplified polynucleotides. The detection/identification of different HPV genotypes is possible because of genotype specific sequence variations in the amplified polynucleotides. This allows distinguishing between different amplified individual polynucleotides. Therefore, the presence or absence of amplified polynucleotides and, therefore, of different HPV genotypes can be assessed by methods and means known in the art which allow the identification of the amplification product(s). This may be done, e.g., by sequencing amplification product (s) and by comparing the resulting sequence to known HPV sequences. Moreover, product(s) may be identified by gel electrophoresis or by RFLP (restriction fragment length polymorphism) analysis. Moreover, the amplified polynucleotides can be determined by methods involving hybridization to poly- or oligonucleotides that are complementary to individual genotypic sequences in the amplified polynucleotides. Such poly- and oligonucleotides are described in the Examples or, e.g., in Schmitt et al., Bead-Based Multiplex Genotyping of Human Papillomaviruses. 2006. J. Clin. Microbiol. 44(2): 504-512, which hereby is incorporated by reference in its entirety, or in van den Brule et al., GP5+/6+ PCR followed by reverse line blot analysis enables rapid and high-throughput identification of human papillomavirus genotypes. 2002. J Clin Microbiol 40:779-87). The hybridization and the detection of the occurrence of a hybridization event may be carried out by any method under any conditions deemed appropriate, e.g., by Southern blot assays, dot blot assays, or by membrane-based reverse line blot (Melchers et al., Prevalence of genital HPV infections in a regularly screened population in The Netherlands in relation to cervical cytology. 1988. J Med Virol 25:11-6; van den Brule et al., GP5+/6+ PCR followed by reverse line blot analysis enables rapid and high-throughput identification of human papillomavirus genotypes. 2002. J Clin Microbiol 40:779-87; Melchers et al., Optimization of human papillomavirus genotype detection in cervical scrapes by a modified filter in situ hybridization test. 1989. J Clin Microbiol 27:106-10). A particularly preferred method for the detection and identification of HPV genotype specific amplification products is a modification of the Multiplex HPV Genotyping (MPG) Assay, as described in Schmitt et al. (loc. cit.): HPV genotype specific probes are coupled to fluorescence-labelled polystyrene beads (Luminex suspension array technology) which are hybridized with the amplification products under suitable, preferably, stringent conditions. Moreover, the amplification products may be identified by use of DNA-Chips which contain HPV genotype specific oligonucleotides linked to a suitable carrier. Additionally, the amplification of an endogenous control polynucleotide and/or an exogenous control polynucleotide may be determined by the methods mentioned above.

The term "contacting" as used in the context of the methods of the present invention is understood by the skilled person. Preferably, the term relates to bringing a composition of the present invention in physical contact with a sample and thereby, e.g. allowing the sample and the composition to interact. Contacting may further involve lysing cells present in the sample and/or the extraction or purification of DNA or RNA.

As set forth above, the composition of the present invention also allows for assessing the viral load in a sample. Therefore, the aforementioned method, preferably, further comprises the step of assessing the viral load of the different HPV genotypes by determining the amount of the different amplified polynucleotides of said HPV genotypes.

Accordingly, the present invention also relates to a method for diagnosing different HPV genotypes and assessing the viral load of different HPV genotypes in a sample of a subject comprising the steps of:
  a) contacting a sample of a subject suspected to comprise different HPV genotypes with the composition according to the invention under conditions which allow for amplification of polynucleotides;
  b) determining the different HPV genotypes based on the amplified polynucleotides obtained in step a); and
  c) assessing the viral load of the different HPV genotypes determined in step b) based on the amount of the different amplified polynucleotides obtained in step a).

Preferably, only the viral load for HPV genotypes that are present in the sample (and, thus, of detected genotypes) is assessed. More preferably, only the viral load of high risk genotypes that are present in the sample is assessed.

The term "viral load" as used herein, preferably, relates to the amount of HPV DNA in a sample of a subject. The assessment of the viral load for specific HPV genotypes that are present in the sample, preferably, is achieved by determining the amounts of the amplified polynucleotides that are specific for the different HPV genotypes. Methods for the determination of the amount of polynucleotides are well known in the art and described, e.g. in the Examples. Preferred methods for the determination of the amounts of polynucleotides are real-time PCR, real-time RT-PCR, real-time NASBA, or signal amplification methods including Hybrid Capture II, bDNA, rolling circle amplification (RCA), and dendrimers.

By determining the viral loads, the severity of an infection with HPV can be assessed.

Therefore, the present invention relates to a method for diagnosing different HPV genotypes and assessing the severity of a HPV infection with different HPV genotypes in a sample of a subject. Preferably, said method comprises the steps of:
  a) contacting a sample of a subject suspected to comprise different HPV genotypes with the composition according to the invention under conditions which allow for amplification of (HPV) polynucleotides;
  b) determining the different HPV genotypes based on the amplified polynucleotides obtained in step a); and
  c) determining the amount of the amplified polynucleotides obtained in step a) of the HPV genotypes as determined in step b)
  d) comparing the amount as determined in step c) with a reference amount, and
  e) assessing the severity of HPV infection.

Steps c) to e) are, preferably, only carried out if at least one HPV genotype is detected in a sample of the subject. More preferably, steps c) to e) are only carried out if at least one high risk HPV genotype is detected in a sample of the subject. Even more preferably steps c) to e) are carried out if at least one of the high risk HPV types 16, 18, 31, 33, 35, 45 is (are) detected in a sample of the subject. Most preferably, steps c) to e) are carried out if HPV16 and/or HPV18 is (are) detected in a sample of the subject.

As used herein, the phrase "assessing the severity of HPV infection", preferably, refers to differentiating between a severe form of HPV16 infection and a mild form of HPV16 infection. As will be understood by those skilled in the art, such an assessment is usually not intended to be correct for 100% of the subjects to be diagnosed. The term, however, requires that a statistically significant portion of subjects can be correctly assessed. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. Preferably, the probability envisaged by the present invention allows that the assessment will be correct for at least 60%, at least 70%, at least 80%, or at least 90% of the subjects of a given cohort or population.

The "mild form of HPV infection" as meant herein, preferably, refers to a form of HPV infection that is histologically classified as normal cervical tissue or as CIN1 (minimal or mild cervical dysplasia), or cytologically classified as NIL/M (negative for intraepithelial lesions or malignancy) or as LSIL (low-grade squamous intraepithelial lesions). Thus, the mild form of HPV infection, preferably, encompasses benign cervical lesions.

A "severe form of HPV infection" as meant herein, preferably, refers to a form of HPV infection that is histologically classified as CIN2 (moderate cervical epithelial dysplasia) or CIN3 (severe cervical dysplasia) or cancerous (in situ or invasive). Accordingly, the term "severe form of HPV16 infection" preferably, refers to a form of HPV16 infection that is cytologically classified as HSIL (high-grade squamous intraepithelial lesions) or cancerous. Thus, the severe form of HPV infection, preferably, encompasses malign cervical lesions.

The term "comparing" as used herein encompasses comparing the amount of the amplified polynucleotide obtained in step a) of the method of the present invention with an amount of a suitable reference source specified elsewhere in this description. It is to be understood that comparing as used herein refers to a comparison of corresponding parameters or values. Preferably, an intensity signal for an amplified polynucleotide of a test sample is compared to the same type of intensity signal of a reference sample. The comparison referred to in step (d) of the aforementioned method of the present invention may be carried out manually or computer-assisted. For a computer-assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step c) and the reference amount, it is possible to assess the severity of a HPV infection in the subject from which the test sample has been obtained. Therefore, the reference amount is to be chosen so that either a difference or a similarity in the compared amounts allows to assess, preferably, whether the subject suffers from a mild form or a severe form of HPV infection (an explanation of the terms "mild form" and "severe form" of HPV infection can be found elsewhere herein)

Accordingly, the term "reference amount" as used herein refers to an amount which allows for assessing the severity of HPV infection, preferably of the severity of infection with a high risk genotype, in a subject. Accordingly, the reference may either be derived from (i) a subject known to suffer from a severe form of HPV infection, or (ii) a subject known to suffer from a mild form of HPV infection. Moreover, the reference amount invention may define a threshold amount whereby an amount of an amplified polynucleotide larger than the threshold shall be indicative for a subject suffering from a severe form of HPV infection, whereas an amount lower than the threshold amount shall be an indicator for a subject suffering from a mild form of HPV infection. A suitable reference amount may be determined by the method of the present invention from a reference sample to be analyzed together, i.e. simultaneously or subsequently, with the test sample. Preferably, the amounts as determined for the test sample and the reference sample are normalized.

Preferably, an amount of an amplified polynucleotide of a HPV genotype larger than the reference amount indicates that the subject suffers from a severe form of HPV infection with said genotype.

Preferably, an amount of an amplified polynucleotide lower than the reference amount indicates that the subject suffers from a mild form of HPV infection.

In one preferred embodiment of the aforementioned method of the present invention the assessment of the severity of HPV infection comprises the steps of:
i) determining the amount of the amplified HPV polynucleotide obtained in step a)
ii) determining the amount of an amplified endogenous control polynucleotide,
iii) calculating a ratio of the amount of said amplified HPV polynucleotide as determined in step i) and the amount of said amplified endogenous control polynucleotide as determined in step ii),
iv) comparing the ratio as calculated in step iii) to a reference ratio, and
v) assessing the severity of HPV infection.

Preferably, the ratio calculated in (iii) is the ratio of the amount of the amplified HPV polynucleotide (as determined in step i)) to the amount of the amplified endogenous control polynucleotide (as determined in step ii)). Preferably, a ratio of the amount of the amplified HPV polynucleotide to the amount of the amplified endogenous control polynucleotide larger than the reference ratio indicates that the subject whose sample is analyzed suffers from a severe form of HPV infection. Preferably, a ratio of the amount of the amplified HPV polynucleotide to the amount of the amplified endogenous control polynucleotide lower than the reference ratio indicates that the subject suffers from a mild form of HPV infection.

Figure 3:
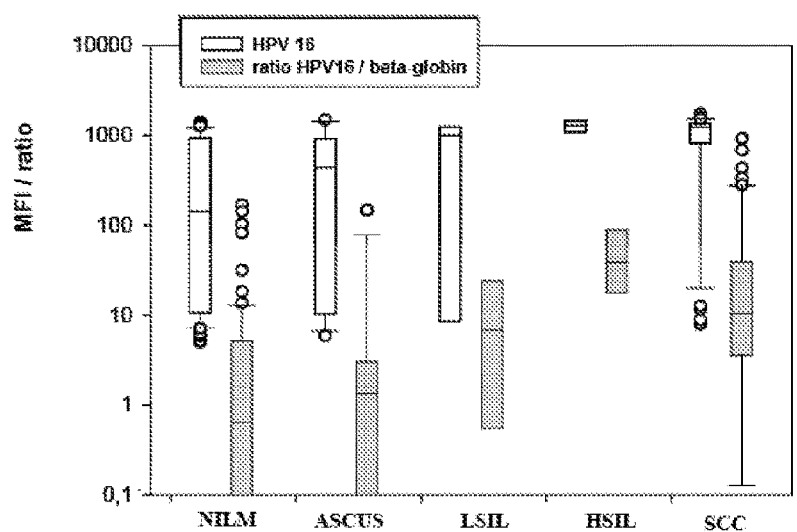
Figure 4:
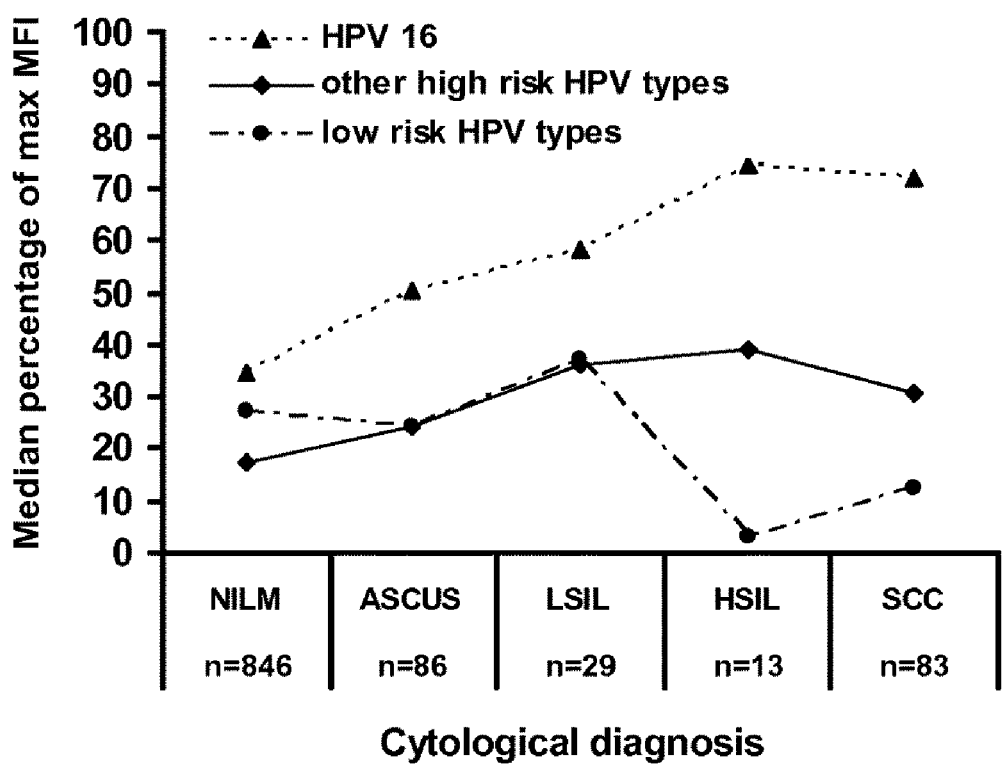

Advantageously, is was shown in the studies underlying the present invention that calculating a ratio of the amount of amplified HPV polynucleotides and amplified endogenous control polynucleotide, and comparing said ratio to a reference ratio, enhances both the sensitivity and specificity of assessing the severity of HPV infection (see Example 8, as well as FIG. 3 and FIG. 4). Specifically, it was shown that in the presence of high HPV quantities (indicating a more severe form of HPV infection) the amplification of the endogenous control polynucleotide is reduced. Thus, an increased viral load in a sample results in an increased amount of amplified HPV polynucleotides and a decreased amount of amplified endogenous control polynucleotides.

Moreover, the present invention relates to the use of the composition according to the present invention for diagnosing various HPV genotypes in a sample of a subject, assessing the viral load of various HPV genotypes and/or the severity of infection with various HPV genotypes.

Finally, the present invention encompasses a kit for carrying out any one of the aforementioned methods of the present invention, wherein said kit comprises a composition according to the invention.

The term "kit" as used herein refers to a collection of the aforementioned means, e.g., means for contacting a sample under conditions which allow for amplification of polynucleotides and for determining different HPV genotypes based on the amplified polynucleotides, preferably, provided separately or within a single container. The container, also preferably, comprises instructions for carrying out the method of the present invention. The components of the kit are provided, preferably, in a "ready-to-use" manner, e.g., concentrations are adjusted accordingly, etc.

All references cited in this specification are herewith incorporated by reference with respect to their entire disclosure content and the disclosure content specifically mentioned in this specification.

The figures show:

FIG. 1. Effect of HPV co-amplification on HPV PCR sensitivity. HPV 16, 39, 66 and 82 plasmids diluted in 100 ng human placenta (HP)-DNA were amplified with oligonucleotides with SEQ ID NOs: 1, 2, 3, 4, 5, 6, 7, 8, 9, 11, 12 and 16, which are subsequently referred to as broad-spectrum general primer PCR (BSGP5+/6+ PCR) with (white) and without (black) b-globin primers, respectively. Dotted line is cut-off for positivity. HPV: human papillomavirus, PCR: polymerase chain reaction, MFI: median fluorescence intensity.

Figure 2:
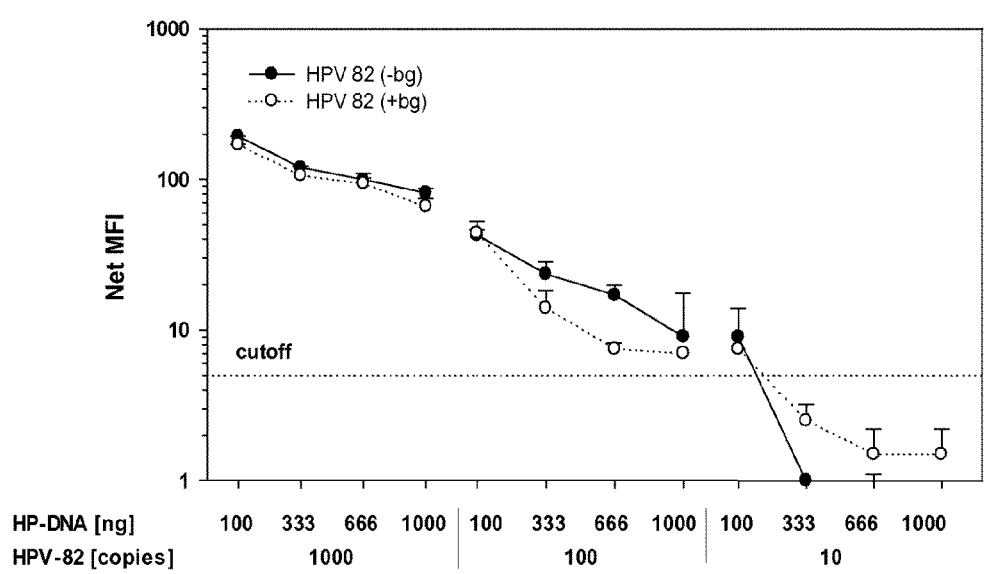

FIG. 2. Analytic sensitivity of BSGP5+/6+ PCR for HPV 82 amplification with different amounts of background DNA. Dilution series of HPV 82 plasmids in 100 to 1,000 ng of human placenta (HP)-DNA, were amplified in the presence (white) and absence (black) of b-globin primers, respectively. Dotted line is cut-off for positivity. HPV: human papillomavirus, MFI: median fluorescence intensity; +bg: simultaneous beta globin amplification; −bg without beta globin amplification; HP: human placenta.

FIG. 3. HPV 16 viral load in cervical exfoliated cells. HPV DNA extracted from 73 samples cytologically diagnosed as "no intraepithelial lesion or malignancy" (NIL/M), 16 samples with "atypical squamous cells of undetermined significance" (ASCUS), 6 samples with "low-grade squamous intraepithelial lesion (LSIL), 6 samples with high-grade squamous intraepithelial lesion (HSIL) and 59 samples with squamous cell carcinoma (SCC) was amplified by BSGP5+/6+ PCR and products were hybridized as described herein. Hybridisation intensities given in median fluorescence intensities (MFI) for HPV 16 positive reactions were presented as box plots grouped by cytological diagnosis. HPV16 values are shown in red and the ratio of HPV 16 versus beta globin signal in grey. The line inside the boxes represents the median and the boxes are delimited by the first and third quartile. Whiskers show the 10 and 90 percentiles. Outliers are shown individually as circles. The 59 HPV 16 DNA-positive samples from a cervical cancer case series were added to the graph to cover the complete spectrum of cervical abnormalities.

FIG. 4: HPV viral load in cervical exfoliated cells. HPV DNA extracted from 846 samples cytologically diagnosed as "no intraepithelial lesion or malignancy" (NIL/M), 86 samples with "atypical squamous cells of undetermined significance" (ASCUS), 29 samples with "low-grade squamous intraepithelial lesion (LSIL), 13 samples with high-grade squamous intraepithelial lesion (HSIL) and 83 samples with squamous cell carcinoma (SCC) was amplified by BSGP5+/6+ and products were hybridized by MPG. Hybridisation intensities were normalized to maximum MFI for each HPV type. Median percentages of max MFI are shown for HPV16 alone, for other high-risk types (18, 31, 33, 35, 39, 45, 51, 52, 56, 58, 59, 68, 73, 82) together and for low-risk types (6, 11, 26, 30, 53, 66, 67, 42, 43, 44, 70) together.

The following Examples shall merely illustrate the invention. They shall not be construed, whatsoever, to limit the scope of the invention.

EXAMPLE 1

HPV Sequence Alignment and HPV Primer Design

The nucleotide sequences of the L1 regions of approximately 50 completely sequenced HPV genotypes, i.e. high-risk HPV 16, 18, 31, 33, 35, 39, 45, 51, 52, 56, 58, 59, 68, 73, 82; putative HR HPV 26, 53 and 66, and LR HPV 6, 7, 11, 13, 30, 32, 34, 40, 42, 43, 44, 54, 55, 61, 62c, 64, 67, 69, 70, 72, 74, 81, 83, 84, 85c, 86c, 87c, 90, 97, 102, 106), were obtained from the National Center for Biotechnology Information (NCBI) nucleotide sequence database (GenBank) and were aligned with T-COFFEE (Notredame, C., D. G. Higgins, and J. Heringa. 2000. T-Coffee: A novel method for fast and accurate multiple sequence alignment. J Mol Biol 302:205-17). The criteria for BSGP5+/6+ primer design were as follows: Pools of oligonucleotides rather than the addition of degenerate base sites in the primer sequences were preferred to avoid synthesis variation in the primer sequence. All primers are targeted to the same region as GP5+/6+. Any HPV type should have I) no more than three mismatches to at least one primer or II) the total number of mismatches in both primers was less or equal than five mismatches. In case of three mismatches to any primer I) the closest mismatch to the 3'end has to follow at least five perfect matching nucleotides. In case of II), primers showing four mismatches to a primer sequence exhibited at least 8 perfect matches between the first mismatch and their 3'end.

HPV sequence alignments with the GP5+/GP6+ primer binding region are shown in Table 1. Moreover, Table 1a lists names, orientations (forward or backward) and nucleic acid sequences of oligonucleotides having a nucleic acid sequence as shown in SEQ ID NOs: 3, 4, 5, 6, 7, 8, 9, 10, 11, and 12. Further included in Table 1a are the sequences of the GP5+ oligonucleotide (SEQ ID NO: 1, forward) and the GP6+ oligonucleotide (SEQ ID NO: 2, backward). The oligonucleotides (forward and backward) listed in Table 1a meet the criteria as defined above. Table 1b lists nucleic acid sequences of additional oligonucleotides that meet said criteria and that have been successfully used for specific amplification of polynucleotides of different HPV genotypes.

TABLE 1

BSGP5+/6+ and GP5+/6+ sequence alignments. HPV sequence alignments with the GP5/GP6+ primer binding region are shown on the left. Nucleotide homology is indicated with a dot, and mismatches are shown with the nucleotide change in the corresponding sequence in upper case. On the right, alignment with best fitting BSGP5+/6+ primers, new mismatches are shown in lower case.

| HPV | Accession number | GP5+ | GP6+ |
|---|---|---|---|
| 6  | X00203    | ....................C..    | ..G..........A..........   |
| 7  | NC_001595 | ........A..T...........    | ..G.T...................   |
| 11 | M14119    | ....................C..    | ..G.T...................   |
| 13 | DQ344807  | ..........A..T.........    | ....T.........A.........   |
| 16 | K02718    | ...........T..T.........   | ........................   |
| 18 | X05015    | ....................C..    | ..........G.............   |
| 26 | NC_001583 | ........CTGT..T.....C..    | ........A.....A.....A....  |
| 30 | X74474    | ..........T..G..C..C..     | ..................G.G....  |
| 31 | J04353    | ....................C..    | ....T.........A......A.... |
| 32 | NC_001586 | ...C.A.....T..G.........   | .........A...........A.... |
| 33 | M12732    | ....................C..    | ..........C........G.....  |
| 34 | NC_001587 | ...T.A.....T...........    | ..G.....CC.G......G.G....  |
| 35 | M74117    | ..........A..T.....A..     | ........................   |
| 39 | M62849    | ...C.......T..G..C.....    | ..G...........A.....A....  |
| 40 | X74478    | ........A..T.....C..C..    | ..G.T......G............   |
| 42 | M73236    | ...T.A........T........    | .........G.G..A.....A....  |
| 43 | AJ620205  | ..........A...........C..  | ........C.G.......A....    |
| 44 | U31788    | ...........T............   | ..G.T...C.....A......G.... |
| 45 | X74479    | ..........A.....C....      | ........................   |
| 51 | M62877    | ...A....CTGT..T.........   | ..G.....A..G..A..........  |
| 52 | X74481    | .....C..A..T..G.....C..    | ....T.........A.........   |
| 53 | X74482    | .....A.....T..G.....C..    | ........A.....A...G.G....  |

TABLE 1-continued

BSGP5+/6+ and GP5+/6+ sequence alignments. HPV sequence alignments with the GP5/GP6+ primer binding region are shown on the left. Nucleotide homology is indicated with a dot, and mismatches are shown with the nucleotide change in the corresponding sequence in upper case. On the right, alignment with best fitting BSGP5+/6+ primers, new mismatches are shown in lower case.

| HPV | Accession number | | |
|---|---|---|---|
| 54 | NC_001676 | ...T.A..A..T........C.. | ....................A.... |
| 55 | U31791 | ..........T............ | ..G.T...C...........G.... |
| 56 | X74483 | ..........A............ | ..........A.....A...G..... |
| 58 | D90400 | ........C.....T......C.. | ..........C.........G..... |
| 59 | X77858 | ...T.A..A..T........... | ......T.......G......A.... |
| 61 | U31793 | .....A..C..T..G.....C.. | ..G.T......G...A..... |
| c62 | AY395706 | ..............G........ | ........T.......G...A.....A.... |
| 66 | U31794 | ..........T..G.......... | ..........AC........G..G.... |
| 67 | D21208 | ...........T.....C..... | ...............G......A.... |
| 68 (ME180) | AJ831568 | ...C......T..G......C.. | ...............G...A.....A.... |
| 68 | X67161 | ...C....C..T..G......A.. | ....................A.... |
| 69 | AB027020 | .........TGT............ | ..........A.........A.... |
| 70 | U22461/U21940 | ...A.........G...C...... | ..........A.........A.... |
| 71 | NC_002644 | .....A...A...T..GACACA.CA | ....T......G...A......A.... |
| 72 | X94164 | .....G...A..T........... | ....T......G...A.... |
| 73 | NC_006165 | ...T.A......T........... | ..G.T...............G..... |
| 74 | AF436130 | ........A..T..G.....C.. | ....T......G...A..... |
| 81 | AJ620209 | ........A.....G......... | ...............G.........C.... |
| 82 | AB027021 | ...A.....TGT..T..C..... | ........A..G..A.....A.... |
| 83 | AF151983 | ........A..T............ | ..........C......G....A...G.. |
| 84 | AF293960 | .....C..G..........C.. | ...............G......A...C.. |
| c85 | AF131950 | ..A.A........C..A... | ..........A.........A.... |
| c86 | AF349909 | ..........C...C...C... | ..............G...A..... |
| c87 | AJ400628 | .....A...G..T..T........ | ............................ |
| CP6108 | U12478 | ................C.. | ..CC.........A..C.. |
| 90 | NC_004104 | .....A........T......... | ....T......G...........C.. |
| 97 | DQ080080 | ...........G..C..A.. | ..G......................... |
| 102 | DQ80083 | .....A...A..T........... | ....................A.....C.... |
| 106 | DQ080082 | .....C..............C.. | ....T......G...A.... |

| HPV | Accession number | BSGP5+/6+ forw. | BSGP5+/6+ backw. |
|---|---|---|---|
| 6 | X00203 | ........................ | ........................ |
| 7 | NC_001595 | ...................c..... | ....T...........a........ |
| 11 | M14119 | ........................ | ....T...........a........ |
| 13 | DQ344807 | ..........A............. | ....T........A.......... |
| 16 | K02718 | ........................ | ........................ |
| 18 | X05015 | ........................ | ............G............ |

TABLE 1-continued

BSGP5+/6+ and GP5+/6+ sequence alignments. HPV sequence alignments with the GP5/GP6+ primer binding region are shown on the left. Nucleotide homology is indicated with a dot, and mismatches are shown with the nucleotide change in the corresponding sequence in upper case. On the right, alignment with best fitting BSGP5+/6+ primers, new mismatches are shown in lower case.

| # | Accession | GP5+/6+ alignment | BSGP5+/6+ alignment |
|---|---|---|---|
| 26 | NC_001583 | ........C..........C.. | ..........g........A.... |
| 30 | X74474 | ...............C..... | ...............G.G.... |
| 31 | J04353 | ...................... | ....T......A.....A.... |
| 32 | NC_001586 | ...C.A................ | ........A........A.... |
| 33 | M12732 | ...................... | ............C....G.... |
| 34 | NC_001587 | .............i........ | ........CC.G..a...G.G.... |
| 35 | M74117 | ..........A....A.. | ...................... |
| 39 | M62849 | ...C...........C..... | ......................A.... |
| 40 | X74478 | ...............C..... | ....T......G..a........ |
| 42 | M73236 | ..........t........... | ..........a........A.... |
| 43 | AJ620205 | ........A............. | ............C.G......A.... |
| 44 | U31788 | ...........T.......... | ....T...C..........G.... |
| 45 | X74479 | ..........A........... | ...................... |
| 51 | M62877 | ...A....C............. | ..G................... |
| 52 | X74481 | .....C..A........ .. | ....T.........A........ |
| 53 | X74482 | .....A................ | ..........g......G.G.... |
| 54 | NC_001676 | ...T.A................ | ...................A.... |
| 55 | U31791 | ...........T.......... | ....T...C.....a.....G.... |
| 56 | X74483 | ..........A........... | ..........g......G..... |
| 58 | D90400 | ........C..t.......... | ............C....G..... |
| 59 | X77858 | ........A.....i....... | ....T......G........A.... |
| 61 | U31793 | .....A..C............. | ....T......G........... |
| c62 | AY395706 | ............G......... | ....T...a..........A.... |
| 66 | U31794 | ...................... | ........AC.......G.G.... |
| 67 | D21208 | ...........T.......... | ..........G........A.... |
| 68 (ME180) | AJ831568 | ...C.................. | ..........a........A.... |
| 68 | X67161 | ...C....C..........A.. | ...................A.... |
| 69 | AB027020 | .............i........ | .........A.........A.... |
| 70 | U22461/U21940 | ....A..........G...... | ............A.....A.... |
| 71 | NC_002644 | .....A..A..T..GACACA.CA | ....T...a..........A.... |
| 72 | X94164 | .....G..A..T.......... | ....T......G........A.... |
| 73 | NC_006165 | .............i........ | ....T......a...G.... |
| 74 | AF436130 | ........A............. | ....T...a.............. |
| 81 | AJ620209 | ........A..t.......... | ...............G........C.... |
| 82 | AB027021 | ...A............C..... | ...................A.... |
| 83 | AF151983 | .............c..... | ........C.....G....A..G. |

TABLE 1-continued

BSGP5+/6+ and GP5+/6+ sequence alignments. HPV sequence alignments
with the GP5/GP6+ primer binding region are shown on the left.
Nucleotide homology is indicated with a dot, and mismatches are shown
with the nucleotide change in the corresponding sequence in upper case.
On the right, alignment with best fitting BSGP5+/6+ primers, new
mismatches are shown in lower case.

| | | | |
|---|---|---|---|
| 84 | AF293960 | .....C..G.............. | ...........G........A..C. |
| c85 | AF131950 | ...A.A..............A.. | ..............A.....A.... |
| c86 | AF349909 | ..............C..C..... | ........a................ |
| c87 | AJ400628 | .....A..G.............. | ......................... |
| CP6108 | U12478 | ....................C.. | ........CC..........A..C. |
| 90 | NC_004104 | .....A........T......... | ....T......G...........C. |
| 97 | DQ080080 | ..............G.....A.. | ..............a.......... |
| 102 | DQ80083 | .....A...........c..... | ..............A.....C.... |
| 106 | DQ080082 | .....C..............C.. | ....T....a............... |

TABLE 1a

Name, orientation, sequence identifier and nucleic
acid sequence of oligonucleotides used for the
detection of HPV genotypes: (bio: biotinylated)

| Oligo-nucleotide Name | Orientation/ Direction | SEQ ID NO | Sequence |
|---|---|---|---|
| GP5+ | Forward | SEQ ID NO: 1 | TTT GTT ACT GTG GTA GAT ACT AC |
| BSGP5+-2 | Forward | SEQ ID NO: 3 | TTT GTT ACT GTT GTI GAT ACT AC |
| BSGP5+-3 | Forward | SEQ ID NO: 4 | TTT GTT ACT GTT GTI GAT ACC AC |
| BSGP5+-4 | Forward | SEQ ID NO: 5 | TTT GTT ACT TGT GTI GAT ACT AC |
| BSGP5+-5 | Forward | SEQ ID NO: 6 | TTT TTA ACT GTT GTI GAT ACT AC |
| BSGP5+-6 | Forward | SEQ ID NO: 7 | TTT GTT ACT GTG GTA GAC ACT AC |
| BSGP5+-7 | Forward | SEQ ID NO: 8 | TTT GTT ACA GTI GTA GAC ACT AC |
| BSGP5+-9 | Forward | SEQ ID NO: 9 | TTT GTT ACT GTG GTA GAT ACC AC |
| BSGP5+-10 | Forward | SEQ ID NO: 10 | TTT GTT ACC GTA GTI GAT ACA AC |
| bio-GP6+ | Backward | SEQ ID NO: 2 | GAA AAA TAA ACT GTA AAT CAT ATT C |
| bio-BSGP6+-b | Backward | SEQ ID NO: 11 | GAA AAA TAA ATT GTA AAT CAT ACT |
| bio-BSGP6+-c | Backward | SEQ ID NO: 12 | GAA AAA TAA ATT GCA ATT CAT ATT |

(I in a sequence stands for Inosine)

TABLE 1b

Name, orientation, sequence identifier and nucleic
acid sequence of oligonucleotides used for the
detection of HPV genotypes, (bio: biotinylated)

| Oligo-nucleotide Name | Orientation/ Direction | SEQ ID NO | Sequence |
|---|---|---|---|
| BSGP5+-8 | Forward | SEQ ID NO: 16 | TTT GTT ACA GTI GTA GAT ACC AC |
| BSGP5+-18 | Forward | SEQ ID NO: 17 | TTT GTT ACC GTG GTI GAT ACC AC |
| bio-BSGP6+-d | Backward | SEQ ID NO: 18 | GAAAAACAAACTGTAGAT CATATTC |
| bio-BSGP6+-e | Backward | SEQ ID NO: 19 | GAAAAATAAATTGTAAAT CAAATTC |
| bio-BSGP6+-f | Backward | SEQ ID NO: 20 | GAAAAATAAACTGTAAAT CAAACTC |
| bio-BSGP6+-g | Backward | SEQ ID NO: 21 | GAAAAATAAACTGCAAAT CAAATTC |
| bio-BSGP6+-h | Backward | SEQ ID NO: 22 | GAAAACAAACTGTAATT CATATTC |

(I in a sequence stands for Inosine)

EXAMPLE 2

Development of Novel b-Globin Primers for the
Amplification of an Endogenous Control
Polynucleotide Different sets of b-globin primer with a length of 20 to 22 nucleotides (Tm: 45-50° C.) were designed with Primer3 (Rozen et al., 2000. Primer3 on the WWW for general users and for biologist programmers. Methods Mol Biol 132:365-86) using the b-globin gene (AY260740) as reference sequence to amplify fragments with 200 to 240 nucleotides in length.

No internal DNA quality control has been described yet for the GP5+/6+ PCR. Instead, different external b-globin PCR serve to control DNA integrity, but thereby cannot control the HPV PCR performance, and the presence and integrity of the DNA in the HPV PCR reaction itself. To redeem that limitation, novel b-globin primers were integrated in the BSGP5+/6+ PCR as well as the standard GP5+/6+ PCR.

To assess the ability of GP5+/6+ or BSGP5+/6+ PCR to co-amplify the DNA quality control b-globin, the CO3/5 primer set (de Roda Husman, A. M., J. M. Walboomers, A. J. van den Brule, C. J. Meijer, and P. J. Snijders. 1995. The use of general primers GP5 and GP6 elongated at their 3' ends with adjacent highly conserved sequences improves human papillomavirus detection by PCR. J Gen Virol 76 (Pt 4):1057-62) and seven newly designed primer pairs (MS1-7fw and MS1-7bw) were tested in various combinations on 10-fold dilutions of plasmids containing genomic DNA from HPV 16, 18, 31 and 33 in a background of 100 ng of Human placenta (HP)-DNA. B-globin and HPV PCR products were visualised by agarose gel electrophoresis. The $CO_{3/5}$ primers failed to co-amplify the b-globin gene. Three combinations of newly designed primers succeeded to amplify the desired PCR fragment. These primer sets were further tested on DNA isolated from HP DNA-containing human cervical carcinoma cells of cell lines SiHa and CaSki, and clinical specimens. Under these conditions, the MS3fw/bw primers amplified PCR fragments visible in the gel. Multiplex detection of b-globin PCR products was achieved through a specific probe included in the MPG assay.

The sequences of the oligonucleotides performing best for the amplification of the endogenous b-globin control polynucleotide sequence are as follows:

```
MS3fw:
AAT ATA TGT GTG CTT ATT TG       (SEQ ID NO: 13)

MS3bw:
AGA TTA GGG AAA GTA TTA GA       (SEQ ID NO: 14)
```

EXAMPLE 3

Amplification of Cloned HPV DNA by GP5+/6+ and BSGP5+/6+ PCR

GP5+/6+ PCR was performed as previously described in WO 95/22626 and de Roda Husman, A. M., J. M. Walboomers, A. J. van den Brule, C. J. Meijer, and P. J. Snijders. 1995. The use of general primers GP5 and GP6 elongated at their 3' ends with adjacent highly conserved sequences improves human papillomavirus detection by PCR. J Gen Virol 76 (Pt 4):1057-62 with some modifications. Briefly, 10 µL of DNA extracted from cervical scrapings or 1 µL of HPV plasmid dilution were amplified in 50 µL containing 50 mM KCl, 0.8 g/L Nonidet™ P40, 10 mM Tris HCl, pH 8.8 (10× PCR buffer, MBI Fermentas GmbH, St. Leon Roth, Germany), 200 µM of each deoxynucleoside triphosphate (dNTP), 3.5 mM $MgCl_2$ (Biozym Scientific GmbH, Hessisch Oldendorf, Germany), 1 U of DNA AmpliTaq polymerase (Roche Applied Biosystems, Mannheim, Germany) and 500 nM each of the GP5+ and 5'-biotinylated GP6+ primers (MWG-Biotech AG, Ebersberg, Germany). In case of the integrated b-globin/GP5+/6+ PCR, 100 nM each of the novel b-globin primers MS3fw and 5'biotinylated MS3bw were added per PCR mixture. A 4 min denaturation step at 94° C. was followed by 40 cycles of amplification with a PCR thermocycler (Gene Amp PCR System 2400, Perkin-Elmer, Wellesley, Mass.) or a Mastercycler (Eppendorf, Germany). Each cycle included a denaturation step at 94° C. for 20 s, an annealing step at 38° C. for 30 s, and an elongation step at 71° C. for 80 s. The final elongation step was prolonged for further 4 min. Ramping rates for the Mastercycler were adjusted as described recently (Snijders, P. J., A. J. van den Brule, M. V. Jacobs, R. P. Pol, and C. J. Meijer. 2005. HPV DNA detection and typing in cervical scrapes. Methods Mol Med 119:101-14): 1.8° C./s from 94° C. to 38° C., 2.0° C./s from 38° C. to 71° C. and 2,8° C./s from 71° C. to 94° C. Each PCR experiment was performed with positive and several negative PCR controls.

For the broad spectrum BSGP5+/6+ PCR assay, 8 additional forward and 2 additional 5'-biotinylated backward primers as shown in SEQ ID NOs: 3, 4, 5, 6, 7, 8, 9, 11, 12 and 16, were added to the GP5+/6+ PCR reaction. 200 nM of each forward (including GP5+), 400 nM of each backward (including GP6+) and 300 nM each of the b-globin primers MS3fw and 5'-biotinylated MS3bw were used. Otherwise, the PCR buffers, reagents and amplification profiles were identical to those described above.

Analytic sensitivity of the BSGP5+/6+ primers, was determined for plasmid clones of HPV 6, 11, 16, 18, 26, 31, 33, 35, 39, 42, 43, 44, 45, 51, 52, 53, 56, 58, 59, 66, 68 (ME180), 70, 73 and 82 (Table 2). Plasmid preparations were quantified using NanoDrop® ND-1000 (NanoDrop Technologies, Wilmington, Del., USA) or a Hitachi U-1100 spectrophotometer (Hitachi, Ltd., Tokyo, Japan). The copy numbers for each HPV type were determined on the basis of the molecular weight of each of the plasmids. 10-fold endpoint dilution series were prepared in 100 ng/µL of Human placenta (HP-) DNA in a total volume of 30 µL. Two to three replicates of each dilution were assayed independently.

After integration of the b-globin primers in both, BSGP5+/6+ and GP5+/6+ PCR, respectively, the analytic sensitivity of both primer sets was compared using PCR, performed in at least duplicates, and MPG using 10-fold dilutions series of plasmids in 100 ng of HP-DNA containing genomic DNA from 24 HPV types (Table 2). Despite b-globin co-amplification, the BSGP5+/6+ primer set amplified all HPV genotypes analysed reaching reproducible levels of sensitivity between 10 and 1,000 copies for all HPV types analysed. The standard GP5+/6+ primers showed more distinct variation in the ability to amplify HPV with detection limits between 10 and 1,000,000 copies. This difference was independent of b-globin co-amplification (see next paragraphs). For HPV 11, 16, 18, 31, 33, 43, 58 and 59 both PCR primer sets demonstrated the same analytic sensitivity. For HPV 6, 35, 42, 45, 52, 70 and 73 the BSGP5+/6+ primer set was at least 10-fold, for HPV 26, 39, 56, 68 (ME180) and 51 100-fold; and for HPV 44, 53 and 82 at least 1,000-fold more sensitive than GP5+/6+. These results showed the improved sensitivity of the novel BSGP5+/6+ primers for these cloned HPV genotypes.

The results of the experiments referred to above are shown in Table 2.

In order to further optimize the amplification of various HPV genotypes, additional experiments using oligonucleotides from Tables 1a and 1b in different combinations resulted in detection limits similar to those listed in Table 2. In comparison to the oligonucleotides with SEQ ID NOs: 1, 2, 3, 4, 5, 6, 7, 8, 9, 11, 12 and 16, the use of an oligonucleotide mixtures comprising oligonucleotides having sequences as shown SEQ ID NOs: 1, 2, 3, 4, 5, 6, 7, 8, 9, 10, 11, and 12, e.g., even improved the detection of the subtype HPV68 (X67161) 10-fold, while the sensitivity of the detection of other types was not changed.

TABLE 2

HPV type detection limits, given in HPV plasmid copy number in 100 ng HP DNA, with different PCR: conventional GP5+/6+ PCR, and GP5+/6+ PCR as well as BSGP5+/6+ PCR both with integrated b-globin PCR.

| HPV type | GP5+6+ | GP5+6+ + b-globin | Broad Spectrum + b-globin | Ratio BS/GP[a] both + b-globin |
|---|---|---|---|---|
| 33[b] |  | 10 | 10 | 1 |
| 58[b] |  | 10 | 10 | 1 |
| 16[c] | 100 | 100 | 100 | 1 |
| 66[c] | 100 | 100 | 100 | 1 |
| 35[b] |  | 100 | 10 | 10 |
| 11[c] | 100 | 100 | 100 | 1 |
| 18[b] |  | 100 | 100 | 1 |
| 31[b] |  | 100 | 100 | 1 |
| 59[b] | 100 | 100 | 100 | 1 |
| 51[c] | 1.000 | 1.000 | 10 | 100 |
| 6[c] | 1.000 | 1.000 | 100 | 10 |
| 42[b] |  | 1.000 | 100 | 10 |
| 45[c] | 1.000 | 1.000 | 100 | 10 |
| 52[b] |  | 1.000 | 100 | 10 |
| 70[c] | 1.000 | 1.000 | 100 | 10 |
| 43[b] |  | 1.000 | 1.000 | 1 |
| 26[b] |  | 10.000 | 100 | 100 |
| 39[c] | 10.000 | 10.000 | 100 | 100 |
| 56[c] | 10.000 | 10.000 | 100 | 100 |
| 68[c] | 10.000 | 10.000 | 100 | 100 |
| 73[c] | 10.000 | 10.000 | 1.000 | 10 |
| 53[b] |  | 100.000 | 100 | 1.000 |
| 82[c] | 100.000 | 100.000 | 100 | 1.000 |
| 44[c] |  | 1.000.000 | 1.000 | 1.000 |

[a] ratio of detection limit BSGP5+/6+ to GP5+/6+, both with b-globin co-amplification
[b] one dilution series, least sensitive detection limit out of quadruplicate PCR indicated
[c] two independent dilution series, least sensitive detection limit out of at least two PCR per dilution series indicated

EXAMPLE 4

Amplification of an Endogenous Control Polynucleotide by b-Globin Specific Oligonucleotides Next, b-globin primer concentration was optimized for integration in BSGP5+/6+ and GP5+/6+ PCR, respectively, with no concurrent competition of HPV PCR. To this end, different amounts of MS3fw/bw b-globin primers were tested on fixed amounts of HPV 16 in a background of HP-DNA. A b-globin primer concentration of 100 nM was used in GP5+/6+ PCR, while 300 nM were used in BSGP5+/6+ PCR to reach similar b-globin signal strengths (data not shown). The respective HPV plus b-globin PCR reached a detection limit of below 10 ng of HP-DNA (approx. 1,700 genome equivalents).

To investigate the effect of b-globin co-amplification on HPV amplification, dilution series of HPV 16, 39, 66 and 82 in constant amount of 100 ng HP-DNA were amplified in duplicates by BSGP5+/6+ PCR with and without b-globin co-amplification, respectively. Irrespective of b-globin co-amplification, HPV detection limits were identical and HPV signal strength showed a high robustness (FIG. 1). In GP5+/6+ PCR, b-globin co-amplification did also not influence the HPV detection limit (data not shown).

To study the effect of increasing amounts of HP-DNA on the HPV detection limit, dilution series of HPV 82 (10 to 1,000 copy numbers) in a background of 100 to 1,000 ng of HP-DNA were examined by BSGP5+/6+ PCR with and without b-globin co-amplification in duplicates. As compared to 100 ng of HP-DNA, amplification of 100 copies of HPV 82 in 1,000 ng of HP-DNA resulted in a fourfold weaker signal. The HPV 82 detection limit rose from 10 to 100 copies when 333 to 1,000 ng of HP-DNA were present (FIG. 2). As compared to BSGP5+/6+ PCR without b-globin primers, the co-amplification of b-globin did not change. HPV 82 detection limit and showed consistent HPV signal strengths when 100 to 1,000 ng of background HP-DNA were used. In total, the ability of the BSGP5+/6+ PCR to detect HPV 82 reciprocally correlated with the amount of background HP-DNA and was independent on b-globin co-amplification.

The results of the experiments referred to above are shown in FIG. 2.

EXAMPLE 5

Evaluation of BSGP5+/6+ PCR with Clinical Samples

For DNA isolation, 2.0 ml (from a total of 20 ml) of cervical scrapings collected with a cytobrush (Cervex-Brush, Rovers Medical Devices B.V., 5347 KV, Holland) in Preserv-Cyt™ solution (Cytyc Corp., Boxborough, Mass., USA) were purified by the Roche High Pure PCR Template Preparation Kit according to the manufacturers' instructions. DNA was eluted in 0.2 ml of elution buffer (10 mM Tris, pH 8.5) and stored at −20° C. until further use. Scrapes were kept 2 months at 4° C. before DNA extraction.

To verify the results of the analyses, we compared BSGP5+/6+ with integrated b-globin PCR, with GP5+/6+ without b-globin PCR on 1112 cervical smears from two different groups. Group 1 comprised a total of 95 cancer patients and group 2 consisted of 1017 women from the general population. To avoid experimental variation both PCR methods were performed in the same PCR run and were analysed on the same plate by Multiplex HPV Genotyping (MPG) for 26 HPV types. Of the 1112 cervical specimens, 27 were excluded, 24 because they were negative for b-globin amplification by BSGP5+/6+ and negative for HPV by both PCR methods. The remaining three samples, strongly typed HPV 16 or 31 positive by GP5+/6+ PCR, were excluded because the BSGP5+/6+ PCR failed to amplify neither beta globin nor HPV.

The general summary for HPV prevalence in the 1085 clinical samples, comprising 93 cervical smears from cancer patients and 992 cervical smears from the general population, is presented in table 3. Altogether the 1085 samples typed for 26 HPV types yielded 28210 typing results for each PCR method. Using 5 net MFI as cut-off, 639 typing results were concordantly positive (2.2%), 28,378 were concordantly negative (96.9%), and 278 were discordant (0.9%), yielding a kappa value of 0.815. This resulted in identical typing of 858 of the 1085 clinical samples (79.1%) and, despite b-globin co-amplification, in an increased overall HPV prevalence of 46.0% by BSGP5+/6+ PCR relative to 41.4% by GP5+/6+ PCR.

Compared to GP5+/6+ PCR, BSGP5+/6+ PCR failed to detect 66 infections but identified 212 additional infections. Table 3 demonstrates the absolute difference in the detection rate of specific HPV types. While some HPV types were systematically better detected by one or the other method only, others showed weak discrepancy with additional weak positivities (below 15 net MFI) by both PCR methods. No difference in detection was found for HPV 6, 26 and 67. HPV 69 was not detected in this study. Weak discrepancies in detection were observed with HPV 11, 16, 18, 33, 35, 43, 45, 56, 59 and 70. The detection of HPV 30, 39, 42, 44, 51, 52, 53, 68 (ME180), 73 and 82 was systematically improved by the BSGP5+/6+ PCR resulting in 1.2- to 9.5-times more frequent detection of these types compared to GP5+/6+ PCR. Additional detections of these types resulted in values above 15 net MFI in at least 50% of cases (table 3) and were found in single as well as multiple infections. Among those additional reactions, also strong BSGP5+/6+ PCR signals (above one third of the maximal HPV probe signal (signal.) observed in this study) were missed by GP5+/6+ PCR: In single as well as multiple infections BSGP5+/6+ PCR additionally detected HPV 82 with signals above one third of signal$_{max}$, HPV 30 and 68(ME180) with signals above half signal$_{max}$, and HPV 44 and 53 with signals equal to signal$_{max}$. Worth mentioning, LR HPV 44 was only detected by BSGP5+/6+ PCR. GP5+/6+ PCR demonstrated better detection of HPV types 31 and 66; showing 1.4- and 1.2-times more frequent detection, respectively. Out of 13 HPV 31 infections additionally detected by GP5+/6+ PCR, seven showed borderline signals with GP5+/6+ PCR (net MFI below 15). The remaining 6 reactions (mean net MFI of 48) were found in multiple infections with at least one concomitant strong infection with one of the following HPV 16, 51, 52, 53, 58 and 59. HPV 66 infections, solely detected by GP5+/6+ PCR, showed borderline values all below 12 net MFI.

A notable difference between the two PCR methods was seen when their abilities to detect specific types as part of multiple infections were compared. The overall proportion of multiple infections detected in HPV-positive samples with the GP5+/6+ PCR was 156 of 449 (34.7%), whereas that with the BSGP5+/6+ PCR was 192 of 499 (38.5%) (Table 4). Among the general population (n=992) the proportion of multiple infections was 16.8% with the BSGP5+/6+ PCR whereas GP5+/6+ PCR found 14.1% multiple positivities. In comparison to the general population, multiple infections were significantly more frequent in cancer patients (n=93) using BSGP5+/6+ PCR (26.9%, p=0.007) while the prevalence was not significantly changed using GP5+/6+ PCR (17.2%, p=0.084%).

The results of the experiments referred to above are shown in Tables 3 and 4.

TABLE 4

Number of HPV negative, single and multiple infections found with BSGP5+/6+ and GP5+/6+ PCR in DNA extracted from 1085 samples of exfoliated cervical cells.

| | | Number of HPV types per sample[a] | | | | | | | | |
|---|---|---|---|---|---|---|---|---|---|---|
| | | 0 | 1 | 2 | 3 | 4 | 5 | 6 | 7 | 8 |
| Cutoff [Net MFI] >5 | BS | 586 | 307 | 108 | 43 | 21 | 10 | 6 | 3 | 1 |
| | GP | 636 | 293 | 103 | 32 | 7 | 2 | 12 | | |

[a]HPV negative (0), single infection (1) to octuple infection (8)

EXAMPLE 6

Optimizing HPV 31 Sensitivity with BSGP5+/6+ PCR

To examine the reason for the apparent lower sensitivity of the BSGP5+/6+ primers for HPV 31, we increased the concentration of the standard GP5+ and GP6+ primers in the BSGP5+/6+ PCR from initially 200 nM to 500 nM and 400 nM to 600 nM, respectively. All 13 clinical samples with multiple infections that were previously HPV 31 negative by BSGP5+/6+ PCR were re-analysed. Comparing initial versus modified BSGP5+/6+ PCR, 7 of 13 previously missed HPV 31 reactions were detected. Amplification of HPV 66 was also optimized resulting in the detection of three out of eight previously BSGP5+/6+ PCR negative infections. The improved detection of HPV types by the initial BSGP5+/6+ PCR was not altered through this modification (data not shown).

TABLE 3

Detection of HPV genotypes within 1085 clinical samples by BSGP5+/6+ or GP5+/6+ PCR followed by MPG

| Typing reaction | Signal Strength | HPV type[a] | | | | | | | | | | | | |
|---|---|---|---|---|---|---|---|---|---|---|---|---|---|---|
| | | 6 | 11 | 16 | 18 | 26 | 30 | 31 | 33 | 35 | 39 | 42 | 43 | 44 | 45 |
| Cutoff [net MFI] >5 | BS only >15 net MFI | | 1[b] | 12 | | | 9 | | | 1 | 7 | 6 | | 11 | 1 |
| | <15 net MFI | | 2 | 25 | 3 | | 1 | | 1 | 3 | 4 | 7 | 1 | | 1 |
| | GP only >15 net MFI | | 1 | 2 | | | | 6 | 2 | 1 | | | | | |
| | <15 net MFI | | 1 | 12 | 3 | | | 7 | 1 | 2 | | | | | 2 |
| | Both | 11 | 16 | 130 | 36 | 8 | 13 | 36 | 29 | 23 | 12 | 27 | 8 | | 23 |
| | Total | 11 | 21 | 181 | 42 | 8 | 23 | 49 | 33 | 30 | 23 | 40 | 9 | 11 | 27 |
| | $r_{BS/GP}$[c] | 0.93 | 0.9 | 1.31 | 0.9 | 1.86 | 33.8 | 0.46 | 0.5 | 0.91 | 2.37 | 4.45 | 0.73 | | 1.04 |

| Typing reaction | Signal Strength | HPV type[a] | | | | | | | | | | | |
|---|---|---|---|---|---|---|---|---|---|---|---|---|---|
| | | 51 | 52 | 53 | 56 | 58 | 59 | 66 | 67 | 68 | 70 | 73 | 82 | total |
| Cutoff [net MFI] >5 | BS only >15 net MFI | 9 | 8 | 24 | 1 | | 1 | | | 11 | | 6 | 10 | 117 |
| | <15 net MFI | 9 | 4 | 10 | 2 | 4 | 2 | | | 4 | 2 | 1 | 8 | 94 |
| | GP only >15 net MFI | | | | | 1 | 2 | | | | 1 | | | 16 |
| | <15 net MFI | 1 | 1 | | 4 | | 3 | 8 | | 2 | 2 | 2 | 1 | 50 |
| | Both | 38 | 28 | 4 | 23 | 29 | 30 | 36 | 13 | 2 | 22 | 24 | 18 | 640 |
| | Total | 57 | 41 | 38 | 30 | 34 | 38 | 44 | 13 | 17 | 27 | 33 | 37 | 922 |
| | $r_{BS/GP}$[c] | 3.46 | 4.93 | 15.1 | 1.05 | 1.77 | 0.75 | 0.53 | 0.61 | 29.3 | 0.89 | 1.76 | 6.03 | |

[a]For sequence accession numbers see Table 1.
[b]Number of positive reactions for given HPV type (above 15 net MFI and below 15 net MFI) using a cutoff >5 net MFI; from 42 total HPV-18 positive samples, 36 were detected by both methods and three additional reactions with values below 15 net MFI were detected by BSGP5+/6+ and GP5+/6+ PCR, respectively. HPV-69 had no positive reaction.
[c]rBS/GP = ratio signal BSGP5+/6+ versus signal GP5+/6+ for double positive reactions.

EXAMPLE 7

Development of an Exogenous Control Polynucleotide

An exogenous control polynucleotide (SEQ ID NO: 15, FIG. 3) was generated by using two elongated primers containing 3'ends that were complementary to a predetermined DNA non-human and non-HPV sequence, here VP1 from murine polyomavirus, a central part that was almost identical to GP5+ and GP6+, respectively, but showed two mismatches to each primer, and a 5'end harbouring restriction enzyme sites for XbaI and EcoRI. PCR reactions were performed with Phusion polymerase and the following protocol: 98° C., 30 s; 35 cycles of 98° C., 30 s; 68° C., 30 s; 72° C. 30 s and final extension at 72° C. for 10 min. The fragment, 144 bp excluding restriction enzyme sites, was cloned into pBluescript KS (−) and controlled by sequencing. After transformation of electro-competent DH5α cells, plasmid DNA was extracted by using Qiagen Plasmid Mini Kit according to the manufacturer's protocol.

Plasmid preparations were quantified using NanoDrop® ND-1000 (NanoDrop Technologies, Wilmington, Del., USA) or a Hitachi U-1100 spectrophotometer (Hitachi, Ltd., Tokyo, Japan). The copy numbers was determined on the basis of the molecular weight of the plasmid. 10-fold endpoint dilution series were prepared in 100 ng/µL of human placenta (HP) DNA in a total volume of 30 µL.

Less than 1,000 copies of the exogenous control polynucleotide were detected by BSGP5+/6+ PCR and subsequent detection by a specific oligonucleotide probe using MPG. No cross-reactivity with other oligonucleotide probes was observed. To control for PCR inhibitors, the internal control can be spiked into the PCR mastermix at low concentration, thereby avoiding competition with HPV amplification.

EXAMPLE 8

Assessing the Severity of Infection with HPV High Risk Genotypes

Viral load of HPV is thought to play an important role in the development of cervical cancer. Large viral loads are considered to be associated with a worse prognosis than low viral loads. It was analyzed whether the composition of the present invention also allows to assess the severity of infection with HPV.

HPV DNA from cervical specimens, including NIL/M, ASCUS, LSIL, HSIL and SCC, was amplified by using a composition of the present invention (oligonucleotides with SEQ ID NOs: 1, 2, 3, 4, 5, 6, 7, 8, 9, 11, 12 and 16). Also included were oligonucleotides which specifically amplify the beta globin gene (oligonucleotides with SEQ ID NO: 13 and SEQ ID NO: 14) Amplification products were hybridized as described elsewhere herein. The results are shown in FIG. 3 and FIG. 4.

In addition to an increase of HPV DNA prevalence with cytological abnormalities, an increase of HPV16 hybridisation signal intensity was observed. MFI values increased from a median of 143 in NILM to 1283 in HSIL and 1242 in cancer cases. Moreover, the ratio of MFI values for HPV16 versus beta-globin increased from NILM to HSIL and decreased again slightly in cervical cancer patients (FIG. 3).

For HPV types other than HPV16, a similar correlation of MFI values to cytological abnormalities was observed. Since HPV probes used in MPG demonstrated different hybridization intensities, HPV signals had to be normalized to the maximum MFI of the respective HPV type. The median percentage of MFI was calculated for HPV16 alone and, due to limitation of positive reactions with other HPV DNA types found in each cytological group, for other high-risk types as well as low-risk types together. The median percentage of MFI of HPV16 increased from NILM (35) to HSIL (74) and slightly decreased again in SCC (72). The pooled other high risk types showed a similar trend but with lower values. In contrast median percentage of maximum MFI values for low-risk types was highest in LSIL (37) and declined in HSIL (3) as well as in SCC (12) group (FIG. 4).

The HPV 16 MFI versus beta-globin MFI ratio was increased with increasing grade of cervical lesion. Similar but weaker increase was also observed for the other high-risk types. The ability of the BSGP5+/6+ PCR with integrated beta globin amplification to assess viral load, can be explained by the fact that high viral loads in high-grade lesions lead to a competition of HPV and beta globin amplification. When HPV amplification reaches saturation due to limitations in DNA polymerase and dNTP quantities before all PCR cycles have been performed, low-affinity primer-mediated amplification of the beta globin gene is reduced in the late PCR cycles. Thus, BS-MPG provides a measure of quantitatively assessing viral load in cervical smears and could be useful in rapidly assessing the grade of cervical dysplasia.

---

The invention claimed is:

1. A composition comprising an oligonucleotide mixture, wherein said oligonucleotide mixture comprises:
   oligonucleotides having the nucleic acid sequences as shown in SEQ ID NO: 1, 2, 3, 4, 5, 6, 7, 8, 9, 10, 11, and 12.

2. The composition of claim 1, wherein the oligonucleotide mixture further comprises oligonucleotides for the amplification of an endogenous control polynucleotide.

3. The composition of claim 1, wherein the oligonucleotide mixture comprises an exogenous control polynucleotide.

4. A method for diagnosing different HPV genotypes in a sample of a subject comprising the steps of
   a) contacting a sample of a subject suspected to comprise different HPV genotypes with the composition of claim 1 under conditions which allow for amplification of polynucleotides; and
   b) determining the different HPV genotypes based on the amplified polynucleotides obtained in step a).

5. The method of claim 4, wherein said composition further comprises oligonucleotides for the amplification of an endogenous control polynucleotide.

6. The method of claim 4, wherein said HPV genotypes are high-risk genotypes.

7. A kit adapted for carrying out the method of claim 4, comprising a composition comprising an oligonucleotide mixture, wherein said oligonucleotide mixture comprises:
   oligonucleotides having the nucleic acid sequences as shown in SEQ ID NO: 1, 2, 3, 4, 5, 6, 7, 8, 9, 10, 11, and 12.

\* \* \* \* \*

SEQUENCE LISTING

<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: Primer/Oligonucleotide

<400> SEQUENCE: 1
tttgttactg tggtagatac tac                                    23

<210> SEQ ID NO 2
<211> LENGTH: 25
<212> TYPE: DNA
<213> ORGANISM: artificial

```
<220> FEATURE:
<223> OTHER INFORMATION: Primer/Oligonucleotide

<400> SEQUENCE: 2
gaaaaataaa ctgtaaatca tattc                                    25

<210> SEQ ID NO 3
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 3
tttgttactg ttgtagatac tac                                      23

<210> SEQ ID NO 4
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 4
tttgttactg ttgtagatac cac                                      23

<210> SEQ ID NO 5
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 5
tttgttactt gtgtagatac tac                                      23

<210> SEQ ID NO 6
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 6
tttttaactg ttgtagatac tac                                      23

<210> SEQ ID NO 7
<211> LENGTH: 23
<212> TYPE: DNA
<213> ORGANISM: artificial
<220> FEATURE:
<223> OTHER INFORMATION: Primer/Oligonucleotide

<400> SEQUENCE: 7
```

```
tttgttactg tggtagacac tac                                              23

<210> SEQ ID NO 8
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (12)..(12)
<223> OTHER INFORMATION: a is Inosine

<400> SEQUENCE: 8
tttgttacag tagtagacac tac                                              23

<210> SEQ ID NO 9
<211> LENGTH: 23
<212> TYPE: DNA
<213> ORGANISM: artificial
<220> FEATURE:
<223> OTHER INFORMATION: Primer/Oligonucleotide

<400> SEQUENCE: 9
tttgttactg tggtagatac cac                                              23

<210> SEQ ID NO 10
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 10
tttgttaccg tagtagatac aac                                              23

<210> SEQ ID NO 11
<211> LENGTH: 25
<212> TYPE: DNA
<213> ORGANISM: artificial
<220> FEATURE:
<223> OTHER INFORMATION: Primer/Oligonucleotide

<400> SEQUENCE: 11
gaaaaataaa ttgtaaatca tactc                                            25

<210> SEQ ID NO 12
<211> LENGTH: 25
<212> TYPE: DNA
<213> ORGANISM: artificial
<220> FEATURE:
<223> OTHER INFORMATION: Primer/Oligonucleotide

<400> SEQUENCE: 12
gaaaaataaa ttgcaattca tattc                                            25

<210> SEQ ID NO 13
<211> LENGTH: 20
<212> TYPE: DNA
<213> ORGANISM: artificial
<220> FEATURE:
<223> OTHER INFORMATION: Primer/Oligonucleotide (for the amplification
      of a control polynucleotide sequence)
```

```
<400> SEQUENCE: 13
aatatatgtg tgcttatttg                                               20

<210> SEQ ID NO 14
<211> LENGTH: 20
<212> TYPE: DNA
<213> ORGANISM: artificial
<220> FEATURE:
<223> OTHER INFORMATION: Primer/Oligonucleotide (for the amplification
      of a control polynucleotide sequence)

<400> SEQUENCE: 14
agattaggga aagtattaga                                               20

<210> SEQ ID NO 15
<211> LENGTH: 144
<212> TYPE: DNA
<213> ORGANISM: artificial
<220> FEATURE:
<223> OTHER INFORMATION: Polynucleotide (additional/internal
      polynucleotide)

<400> SEQUENCE: 15
tttgttacag ttgtagatac taccaattag caaggccaag ctggataagg acggaatgta   60
tccagttgaa atctggcatc cagatccagc aaaaaatgag aacacaaggt actttggcag  120
aatatgattt acagtttatt tttc                                         144

<210> SEQ ID NO 16
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (12)..(12)
<223> OTHER INFORMATION: a is Inosine

<400> SEQUENCE: 16
tttgttacag tagtagatac cac                                           23

<210> SEQ ID NO 17
<211> LENGTH: 23
<212> TYPE: DNA
<213> ORGANISM: artificial
<220> FEATURE:
<223> OTHER INFORMATION: Primer/Oligonucleotide
<220> FEATURE:
<221> NAME/KEY: modified_base
<222> LOCATION: (15)..(15)
<223> OTHER INFORMATION: a is Inosine

<400> SEQUENCE: 17
tttgttaccg tggtagatac cac                                           23

<210> SEQ ID NO 18
<211> LENGTH: 25
<212> TYPE: DNA
<213> ORGANISM: artificial
<220> FEATURE:
<223> OTHER INFORMATION: Primer/Oligonucleotide

<400> SEQUENCE: 18
gaaaaacaaa ctgtagatca tattc                                         25

<210> SEQ ID NO 19
```

```
<211> LENGTH: 25
<212> TYPE: DNA
<213> ORGANISM: artificial
<220> FEATURE:
<223> OTHER INFORMATION: Primer/Oligonucleotide

<400> SEQUENCE: 19
gaaaaataaa ttgtaaatca aattc                                         25

<210> SEQ ID NO 20
<211> LENGTH: 25
<212> TYPE: DNA
<213> ORGANISM: artificial
<220> FEATURE:
<223> OTHER INFORMATION: Primer/Oligonucleotide

<400> SEQUENCE: 20
gaaaaataaa ctgtaaatca aactc                                         25

<210> SEQ ID NO 21
<211> LENGTH: 25
<212> TYPE: DNA
<213> ORGANISM: artificial
<220> FEATURE:
<223> OTHER INFORMATION: Primer/Oligonucleotide

<400> SEQUENCE: 21
gaaaaataaa ctgcaaatca aattc                                         25

<210> SEQ ID NO 22
<211> LENGTH: 25
<212> TYPE: DNA
<213> ORGANISM: artificial
<220> FEATURE:
<223> OTHER INFORMATION: Primer/Oligonucleotide

<400> SEQUENCE: 22 gaaaacaaa ctgtaattca tattc                                          25
```